(12) United States Patent
Sauer

(10) Patent No.: US 12,016,551 B2
(45) Date of Patent: Jun. 25, 2024

(54) CRIMPING INSTRUMENT AND LOADING TOOL THEREFOR

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 424 days.

(21) Appl. No.: 17/604,574

(22) PCT Filed: Apr. 24, 2020

(86) PCT No.: PCT/US2020/029686
§ 371 (c)(1),
(2) Date: Oct. 18, 2021

(87) PCT Pub. No.: WO2020/219790
PCT Pub. Date: Oct. 29, 2020

(65) Prior Publication Data
US 2022/0192658 A1     Jun. 23, 2022

Related U.S. Application Data

(60) Provisional application No. 62/838,250, filed on Apr. 24, 2019.

(51) Int. Cl.
*A61B 17/04*     (2006.01)

(52) U.S. Cl.
CPC ...... *A61B 17/0487* (2013.01); *A61B 17/0469* (2013.01); *A61B 2017/0488* (2013.01)

(58) Field of Classification Search
CPC ............ A61B 17/0487; A61B 17/0469; A61B 2017/0488; A61B 17/0485
See application file for complete search history.

(56) References Cited

U.S. PATENT DOCUMENTS 5,643,289 A * 7/1997 Sauer ................ A61B 17/1285
                                     606/147
5,693,059 A * 12/1997 Yoon ................ A61B 17/12013
                                     606/139

(Continued)

FOREIGN PATENT DOCUMENTS

| CA | 3076132 | 6/2016 |
|---|---|---|
| JP | 2005-507690 | 3/2005 |

OTHER PUBLICATIONS

PCT International Preliminary Report on Patentability, International Application No. PCT/US2020/029686, filed Apr. 20, 2020, 6 pages.

(Continued)

*Primary Examiner* — Julian W Woo
(74) *Attorney, Agent, or Firm* — Michael E. Coyne

(57) ABSTRACT

An instrument for crimping one or more suture fasteners to one or more corresponding surgical sutures is disclosed. The instrument also includes at least one shaft having one or more receiving faces, one or more anvils, one or more hammers, one or more pushers moveable in a direction substantially parallel to a longitudinal axis of the at least one shaft and configured to engage at least one of the hammer and the anvil for urging the hammer and the anvil together; and a loading tool. The loading tool may also include a target cover defining one or more snare guides, a target tray coupled to the target cover, one or more suture fasteners, one or more snare loops, and at least one handle.

22 Claims, 30 Drawing Sheets

(56) References Cited

U.S. PATENT DOCUMENTS

| | | | | |
|---|---|---|---|---|
| 7,235,086 | B2* | 6/2007 | Sauer | A61B 1/0014 |
| | | | | 606/151 |
| 9,943,303 | B2* | 4/2018 | Sauer | A61B 17/06166 |
| 10,016,193 | B2* | 7/2018 | Smith | A61B 17/0469 |
| 2003/0204205 | A1 | 10/2003 | Sauer | |
| 2004/0097908 | A1 | 5/2004 | Shikhman et al. | |
| 2007/0129719 | A1 | 6/2007 | Kendale et al. | |
| 2016/0007986 | A1 | 1/2016 | Sauer | |
| 2016/0166248 | A1 | 6/2016 | Deville et al. | |
| 2016/0220238 | A1 | 8/2016 | Heneveld | |
| 2016/0345956 | A1 | 12/2016 | Sauer | |
| 2018/0103944 | A9 | 4/2018 | Sauer | |
| 2018/0177503 | A1 | 6/2018 | Miraki | |

OTHER PUBLICATIONS

Extended European Search Report, Application No. 20795670.7 dated Nov. 11, 2022, 9 pages.

* cited by examiner

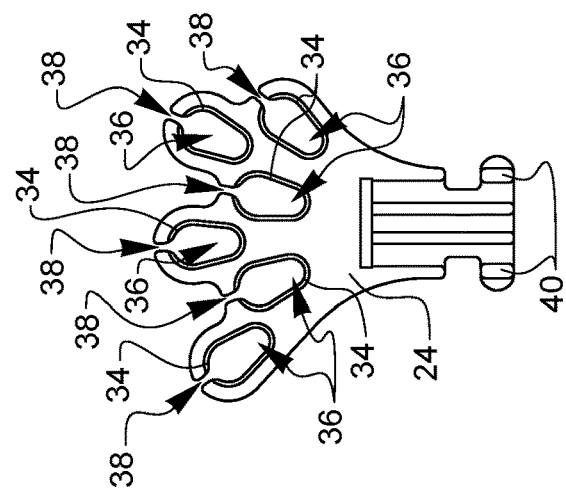
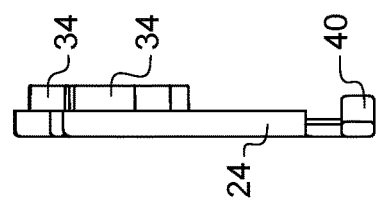
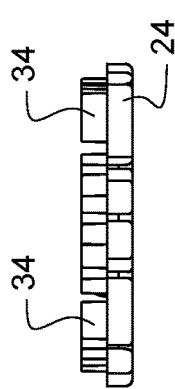
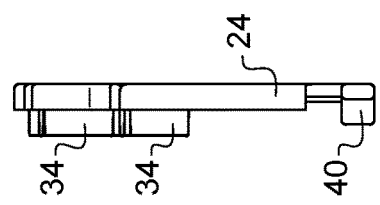
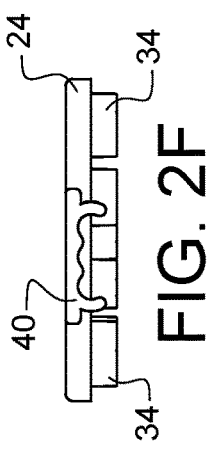

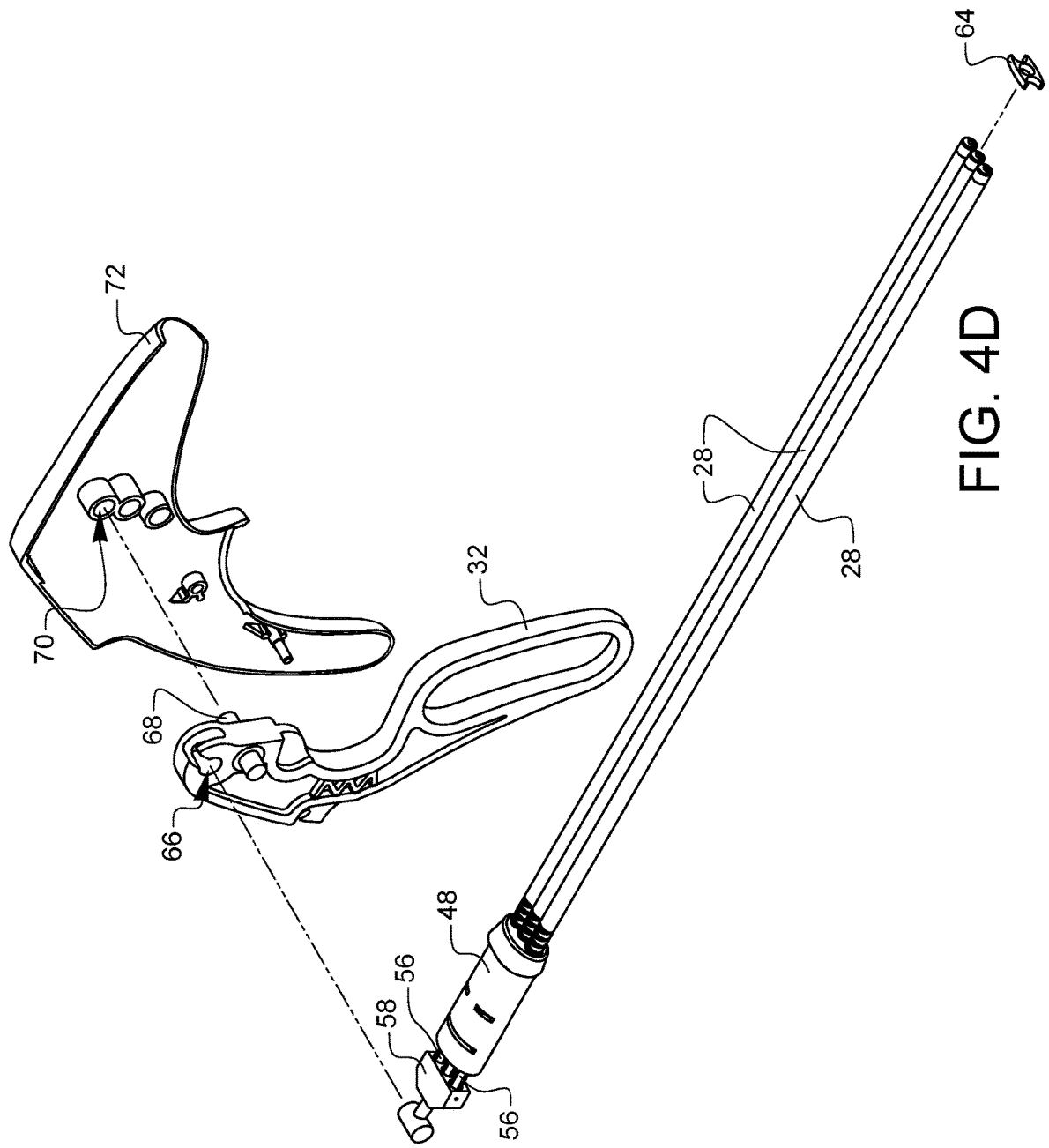

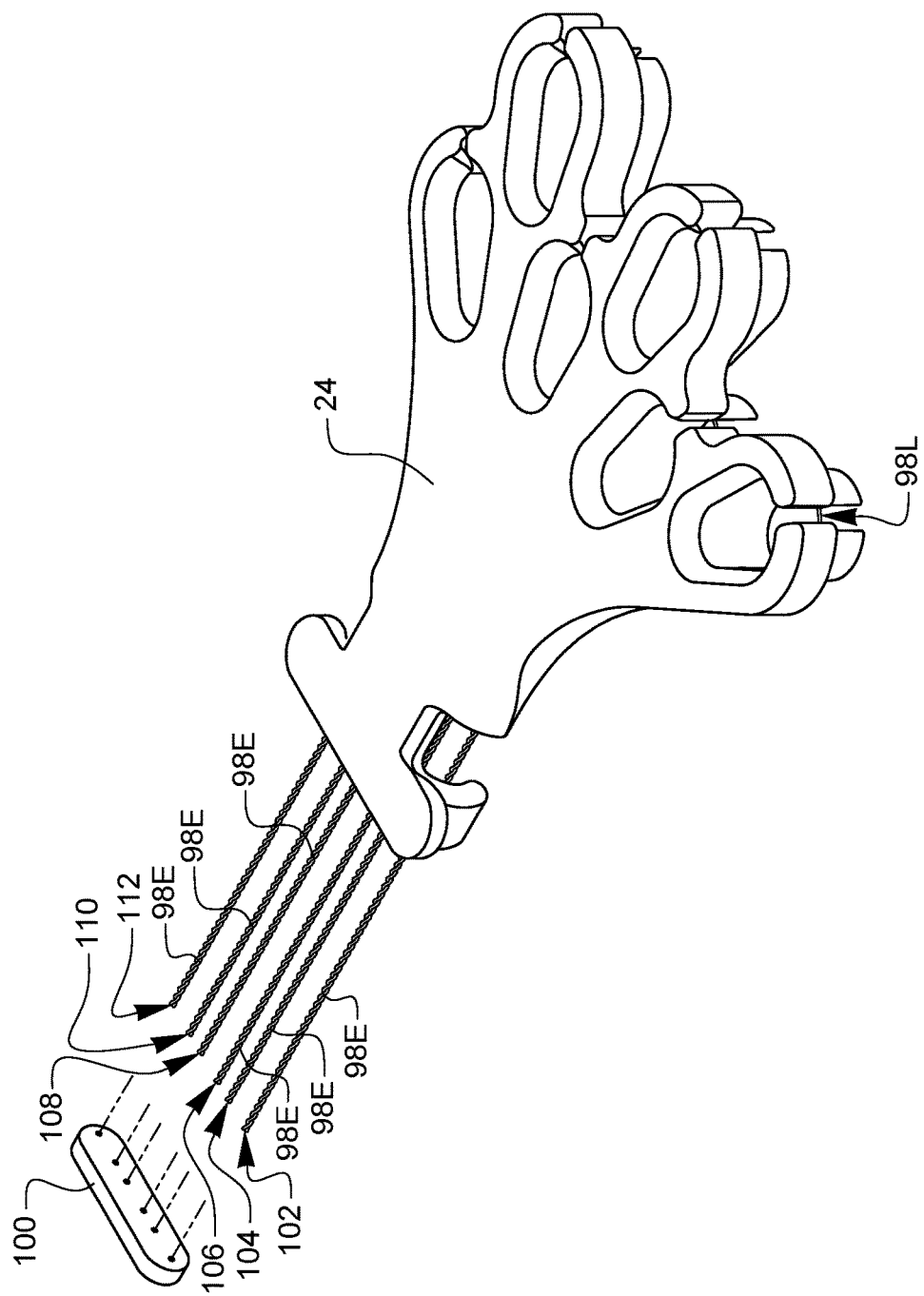

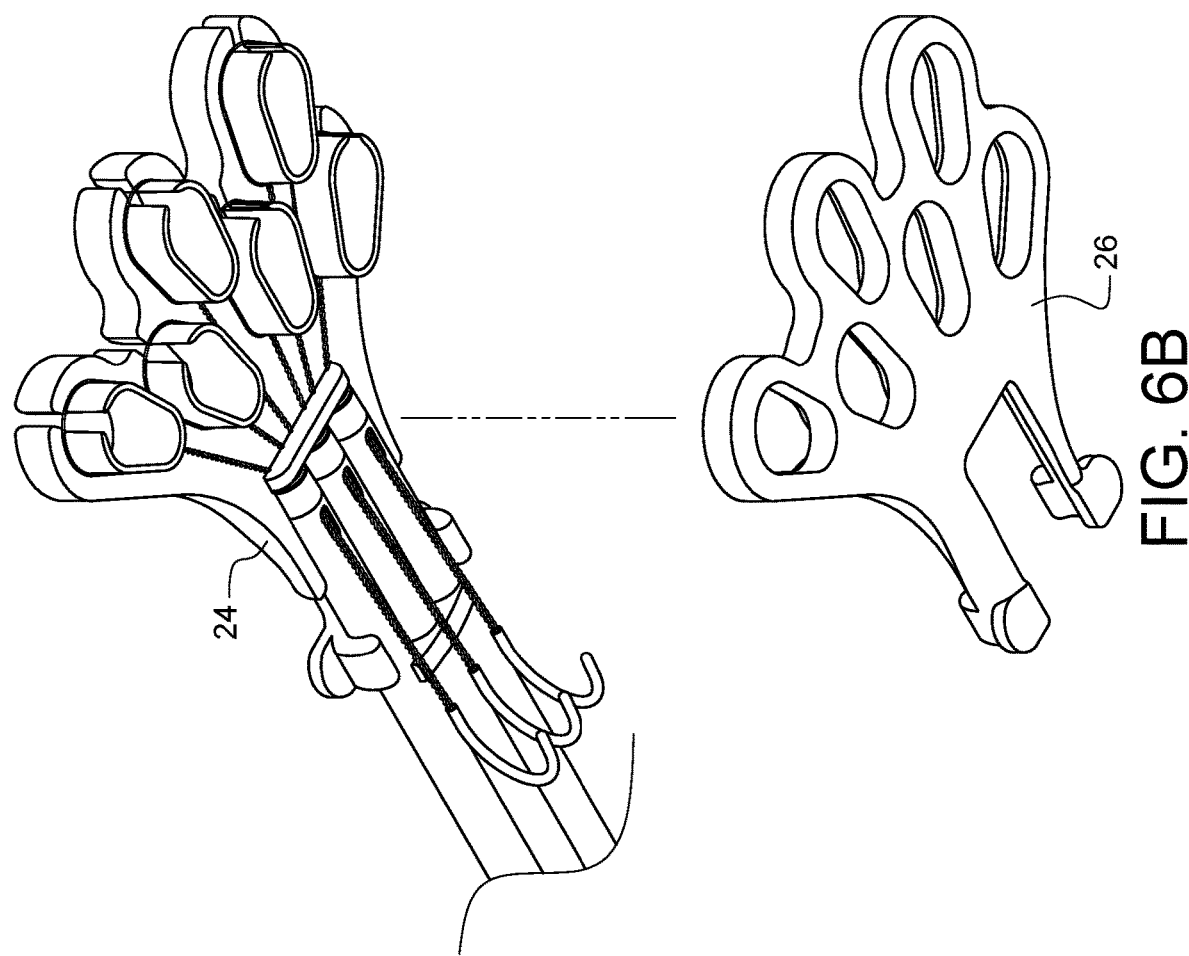

CRIMPING INSTRUMENT AND LOADING TOOL THEREFOR

RELATED APPLICATIONS

This application is a national stage application, filed under 35 U.S.C. § 371, of International Patent Application No. PCT/US20/29686, filed Apr. 24, 2020 and entitled "CRIMPING INSTRUMENT AND LOADING TOOL THEREFOR," which claims priority to U.S. Provisional Patent Application No. 62/838,250, filed Apr. 24, 2019 and entitled "CRIMPING INSTRUMENT AND LOADING TOOL THEREFOR," each of which is hereby incorporated by reference in its entirety.

FIELD

The claimed invention relates generally to surgical instruments for crimping a sleeve to a secured suture, and more particularly to such a surgical instrument having a loading tool therefor.

BACKGROUND

Malleable suture fasteners such as the sleeves sold under the trademarks Ti-KNOT® and COR-KNOT® by LSI Solutions, Inc. are a significant improvement over hand or instrument-tied knots in laparoscopic surgical procedures. The sleeves, which are made of a malleable material, for example titanium, that has proven safe with prolonged exposure to body tissue, are slid over two or more strands of suture and deformed or crimped to secure the strands of suture.

An exemplary crimping instrument is shown in U.S. Pat. No. 7,235,086, entitled "CRIMPING INSTRUMENT WITH MOTION LIMITING FEATURE", assigned to LSI Solutions, Inc., of Victor, N.Y. With such a device, suture ends can be threaded through a crimping sleeve held between a hammer and an anvil in the end of the device. The suture ends pass out a hole in the side of the shaft, and the device can be used to position the crimping sleeve at a desired location on the suture relative to a surface through which the suture has been secured (for example, tissue, a replacement anatomical structure such as a heart valve, or an augmentative anatomical structure such as a heart valve annulus).

An actuator causes a wedge, located in the shaft, to advance and to force the hammer into the crimping sleeve. The hammer crimps the crimping sleeve against the anvil, and the suture is held tightly by the deformed sleeve. A blade may also be incorporated within the shaft and can be simultaneously moveable by the actuator in order to trim the suture ends.

Such instruments for attaching suture fasteners have proven to be very effective. The Ti-KNOT® and COR-KNOT® devices from LSI Solutions, Inc. (information available at www.lsisolutions.com) have been widely accepted by surgeons for the recognized benefits of time savings, ease of use, and reliability. (See, for example, "New Knot Tying Technique for Minimally Invasive Approach to Mitral Valve Repair", an abstract by Rodriguez, Sutter, and Ferdinand presented at the AATS 2011 Mitral Conclave in New York, N.Y. in 2011 or "Use of Automatic Knot-Tying and Cutting Device is Shortening Aortic Cross-Clamp Times in Minimally Invasive Mitral Valve Surgery", an abstract by Gersak and Robic presented at the 26th Annual EACTS Meeting in Barcelona, Spain in 2012.)

Devices like the COR-KNOT® device enable many types of minimally invasive surgery (MIS), or, more specifically, minimally invasive cardiac surgery (MICS). MIS is a type of surgery performed through one or more small incisions or access sites created in a patient. MIS has been shown to have at least equivalent morbidity and mortality outcomes as compared to conventional approaches, with reported advantages of reduced postsurgical pain, better respiratory function, shorter hospital stay, and improved cosmesis.

Typically, for crimping instruments like the COR-KNOT® device, a quick load unit is provided to facilitate the loading of the crimpable sleeve into the device and then the suture through the crimpable sleeve held by the device. While this works well for single crimpable fasteners at a time when used with a single pair of suture ends, it does not lend itself to use with multiple sets of suture ends, especially when pledgets are involved. Such scenarios are further complicated by the further need for crimping devices which are capable of handling multiple crimpable fasteners at the same time.

Therefore, not only is there a need for a surgical crimping instrument capable of placing multiple crimpable fasteners at the same time, there is also a need for a loading tool for surgical crimping instruments that is compatible with multiple sets of suture ends, multiple crimpable fasteners, and the inherent need for suture management which arises with such use, especially when pledgets are involved. Furthermore, there is a need for such a loader, whether separate from a crimping instrument or integral with a crimping instrument to be simple to use.

SUMMARY

An instrument for crimping one or more suture fasteners to one or more corresponding surgical sutures is disclosed. The instrument also includes at least one shaft; one or more receiving faces, each configured to receive one of the one or more suture fasteners; one or more anvils, each of the one or more anvils corresponding to one of the one or more receiving faces; one or more hammers, each of the one or more hammers corresponding to one of the one or more anvils and moveable relative to its corresponding anvil for crimping the one or more suture fasteners therebetween and received in the one or more receiving faces; one or more pusher moveable in a direction substantially parallel to a longitudinal axis of the at least one shaft and configured to engage at least one of the hammer and the anvil for urging the hammer and the anvil together; and a loading tool, may include: a target cover defining one or more snare guides; a target tray coupled to the target cover; one or more suture fasteners, each of the one or more suture fasteners located within a corresponding one of the one or more receiving faces of the instrument; one or more snare loops, each wrapped around a corresponding one of the one or more snare guides; and at least one handle coupled to the one or more snare loops such that movement of the at least one handle draws the one or more snare loops to which it is coupled through one or more of the suture fasteners.

A loading tool for a crimping instrument is also disclosed. The loading tool also includes a target cover defining one or more snare guides; a target tray coupled to the target cover; one or more suture fasteners; one or more snare loops, each wrapped around a corresponding one of the one or more snare guides; and at least one handle coupled to the one or more snare loops such that movement of the at least one handle relative to the one or more suture fasteners draws the one or more snare loops to which the at least one handle is coupled through one or more of the suture fasteners.

BRIEF DESCRIPTION OF THE DRAWINGS

FIGS. 2A, 2B, 2C, 2D, 2E, and 2F are top, left, right, bottom, distal, and proximal views, respectively, of one embodiment of a target cover from the loading tool of FIG. 1A.

FIGS. 6A-6C are partially exploded views illustrating another embodiment of a loading tool for a surgical crimping instrument.

Figure 1A:
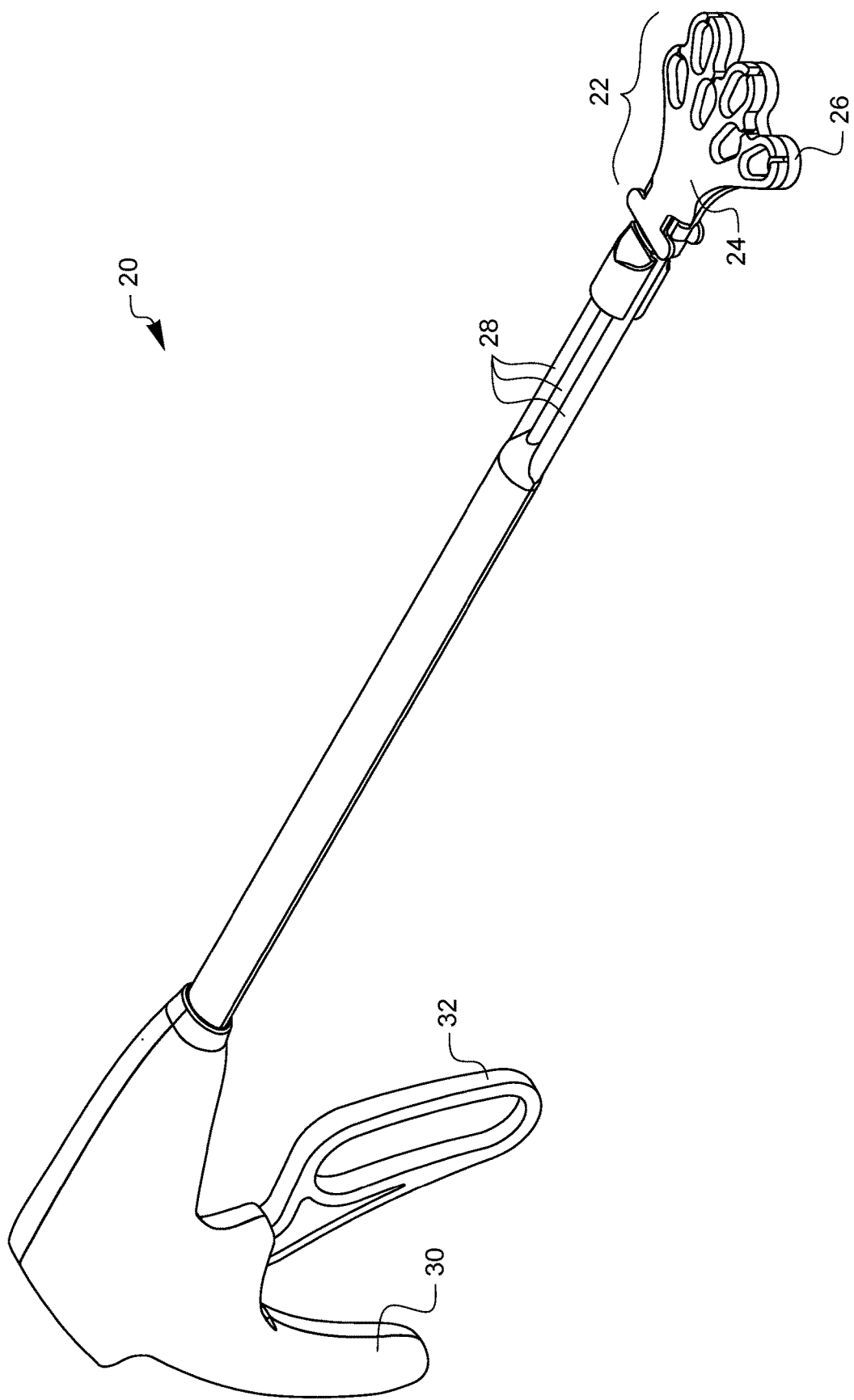
FIG. 1A is a top-right-distal perspective view of one embodiment of an instrument for crimping suture fasteners having one embodiment of a loading tool.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 1B:
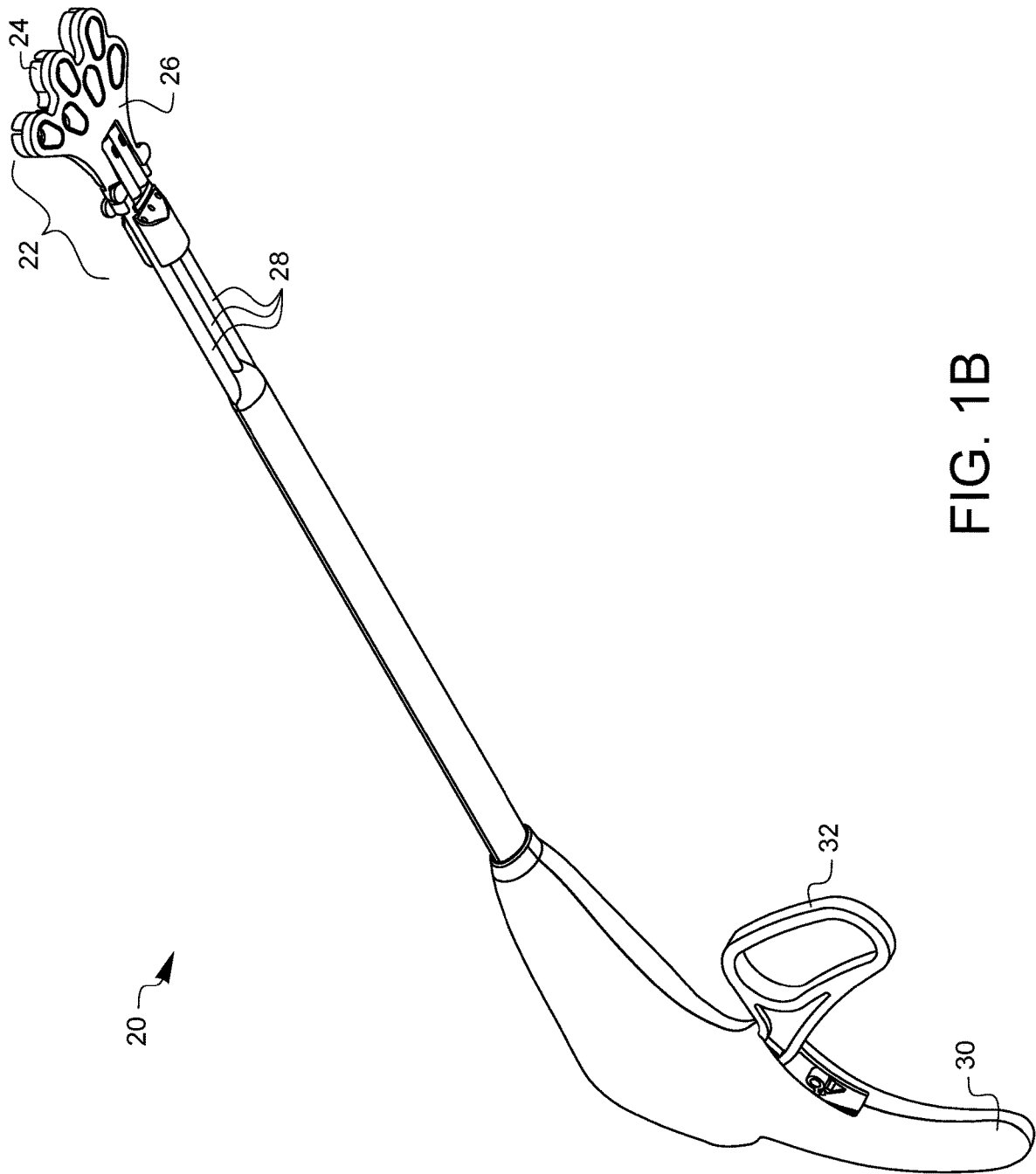
FIG. 1B is a bottom-right-distal perspective view of the crimping instrument and loading tool of FIG. 1A.
Figure 3D:
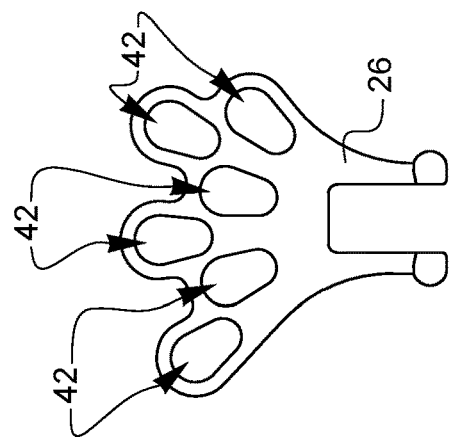
FIGS. 3A, 3B, 3C, 3D, 3E, and 3F are top, left, right, bottom, distal, and proximal views, respectively, of one embodiment of a target tray from the loading tool of FIG. 1A.
Figure 3C:
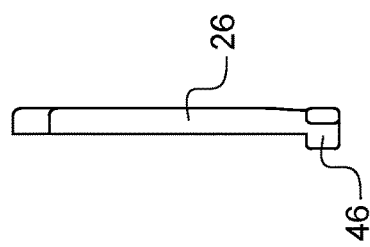
Figure 3E:
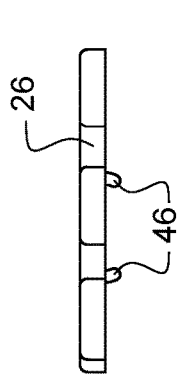
Figure 3A:
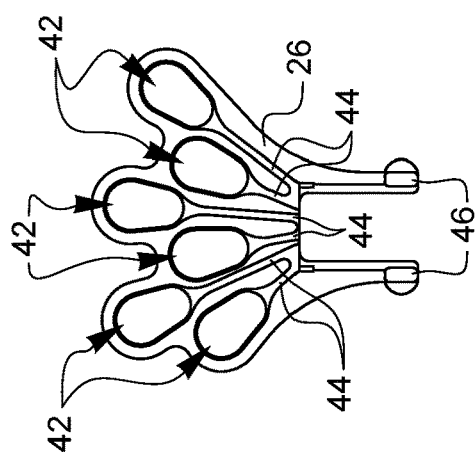
Figure 3F:
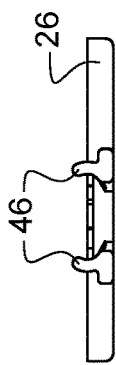
Figure 3B:
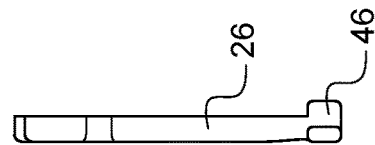

FIG. 1A is a top-right-distal perspective view of one embodiment of an instrument 20 for crimping suture fasteners having one embodiment of a loading tool 22. FIG. 1B is a bottom-right-distal perspective view of the crimping instrument 20 and loading tool 22 of FIG. 1A. The loading tool 22 has a target cover 24 and a target tray 26.

In this embodiment, the crimping instrument 20 has a plurality of shafts 28, the distal ends of which each hold a receiving face (not visible in this view, but discussed below) configured to receive a suture fastener. The crimping instrument also has a handle 30 which the user can hold and a lever 32 which is moveable relative to the handle 30 for actuating structures within the instrument 20 for crimping the suture fasteners held by the device when desired. The structures which make this possible will be discussed in more detail below.

FIGS. 2A, 2B, 2C, 2D, 2E, and 2F are top, left, right, bottom, distal, and proximal views, respectively, of one embodiment of a target cover 24 from the loading tool 22 of FIG. 1A. The target cover 24 defines a plurality of snare guides 34. The target cover 24 also defines a plurality of suture openings 36, each of which lies at least partially within a corresponding one of the one or more snare guides 34. The target cover 24 further defines a suture clearance slot 38 coupled to (or in communication with) each of the one or more target cover suture openings 36. The target cover 24 also has a coupling latch 40.

FIGS. 3A, 3B, 3C, 3D, 3E, and 3F are top, left, right, bottom, distal, and proximal views, respectively, of one embodiment of a target tray 26 from the loading tool 22 of FIG. 1A. The target tray 26 defines a plurality of suture openings 42. The target tray 26 of this embodiment also defines a plurality of snare channels 44. The target tray 26 also has a coupling latch 46.

Figure 4A:
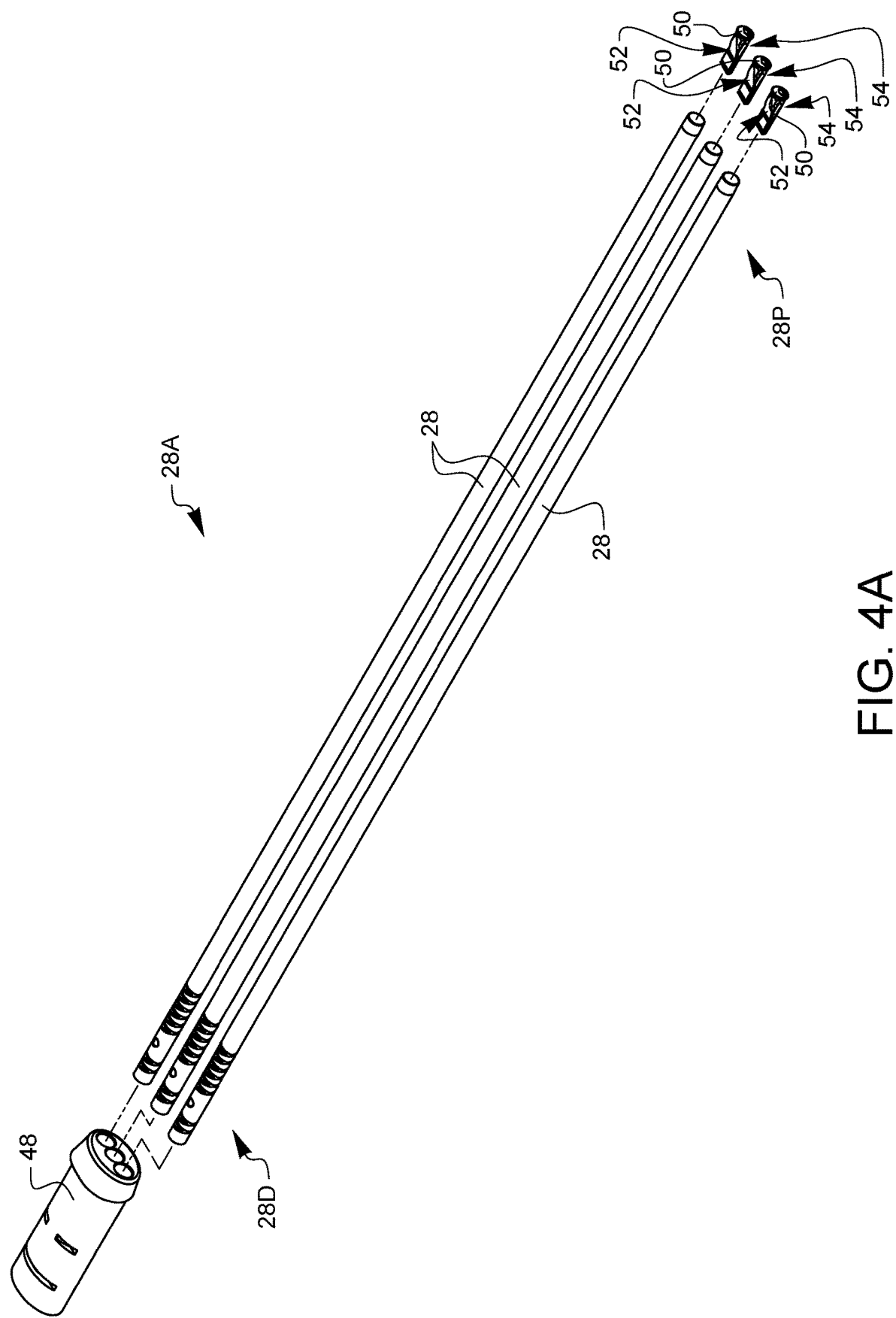
FIGS. 4A-4P are a series of exploded views which illustrate the assembly of one embodiment of a crimping instrument having a loading tool. Note that there are no FIGS. 4I and 4O to avoid possible confusion with similar looking numbers.
Figure 4B:
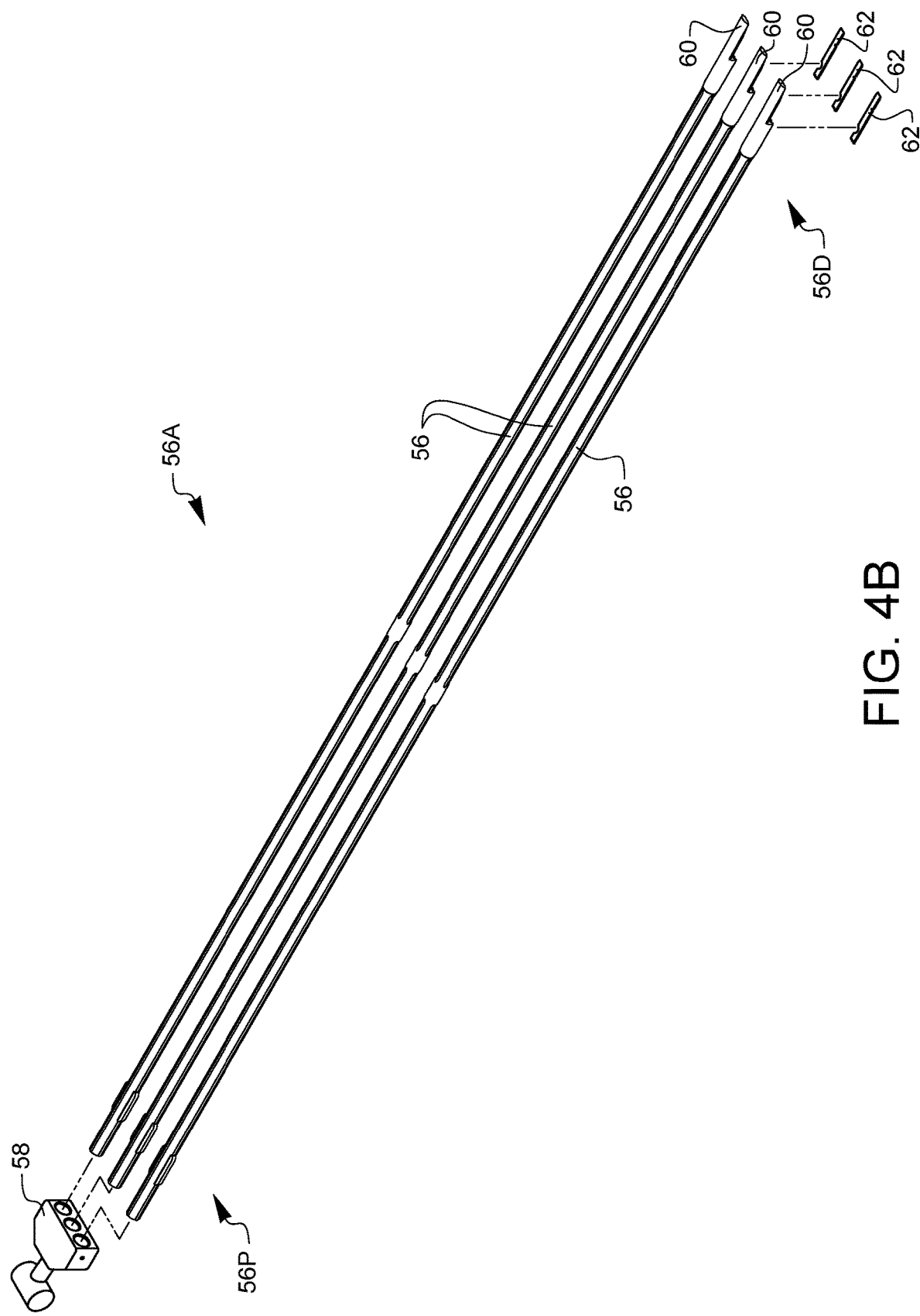
Figure 4C:
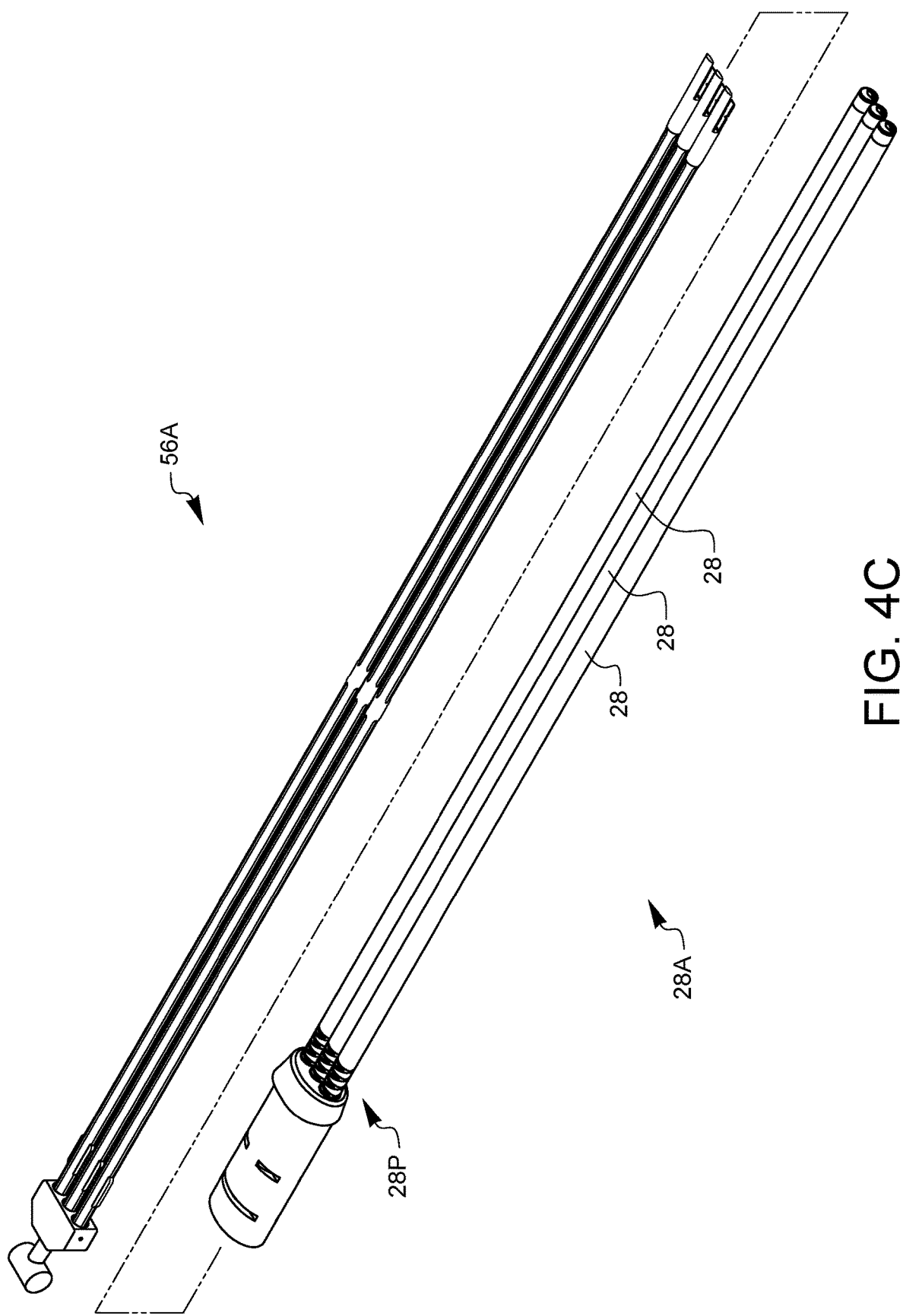
Figure 4E:
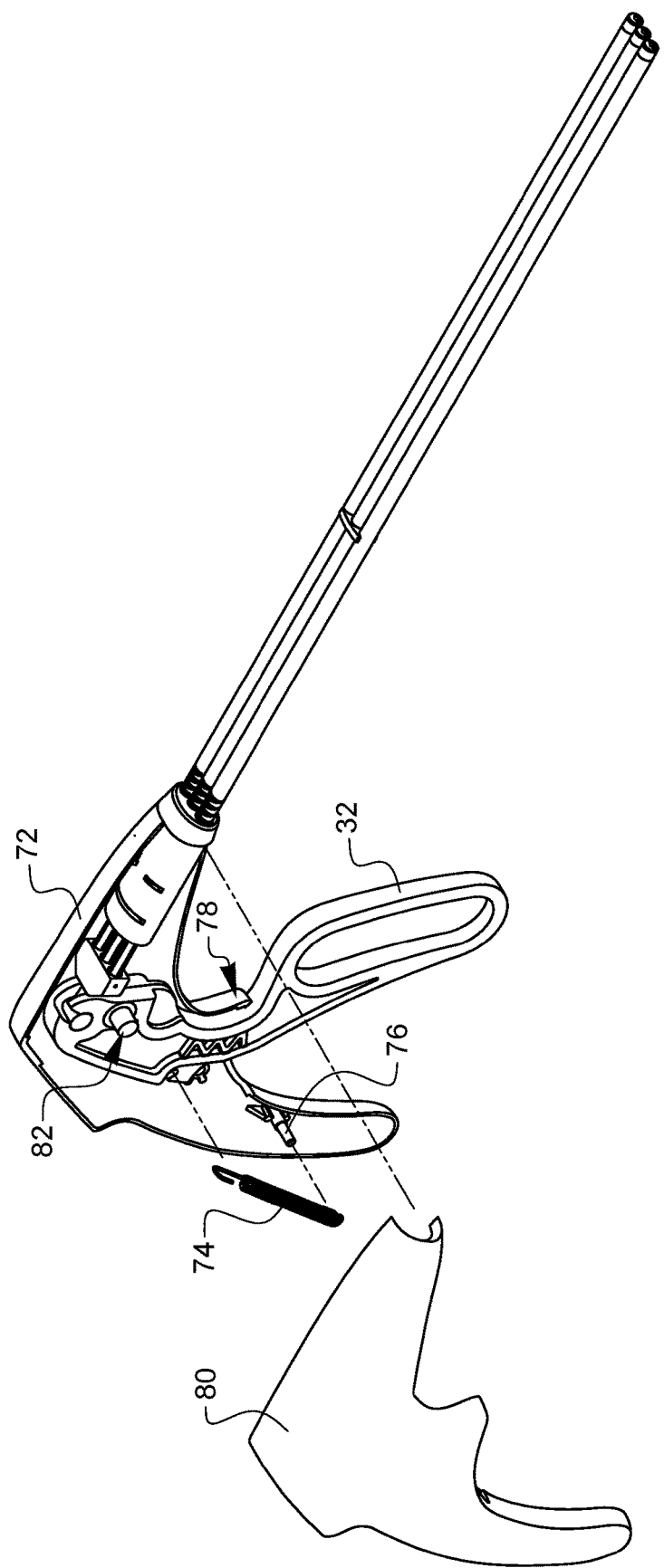
Figure 4F:
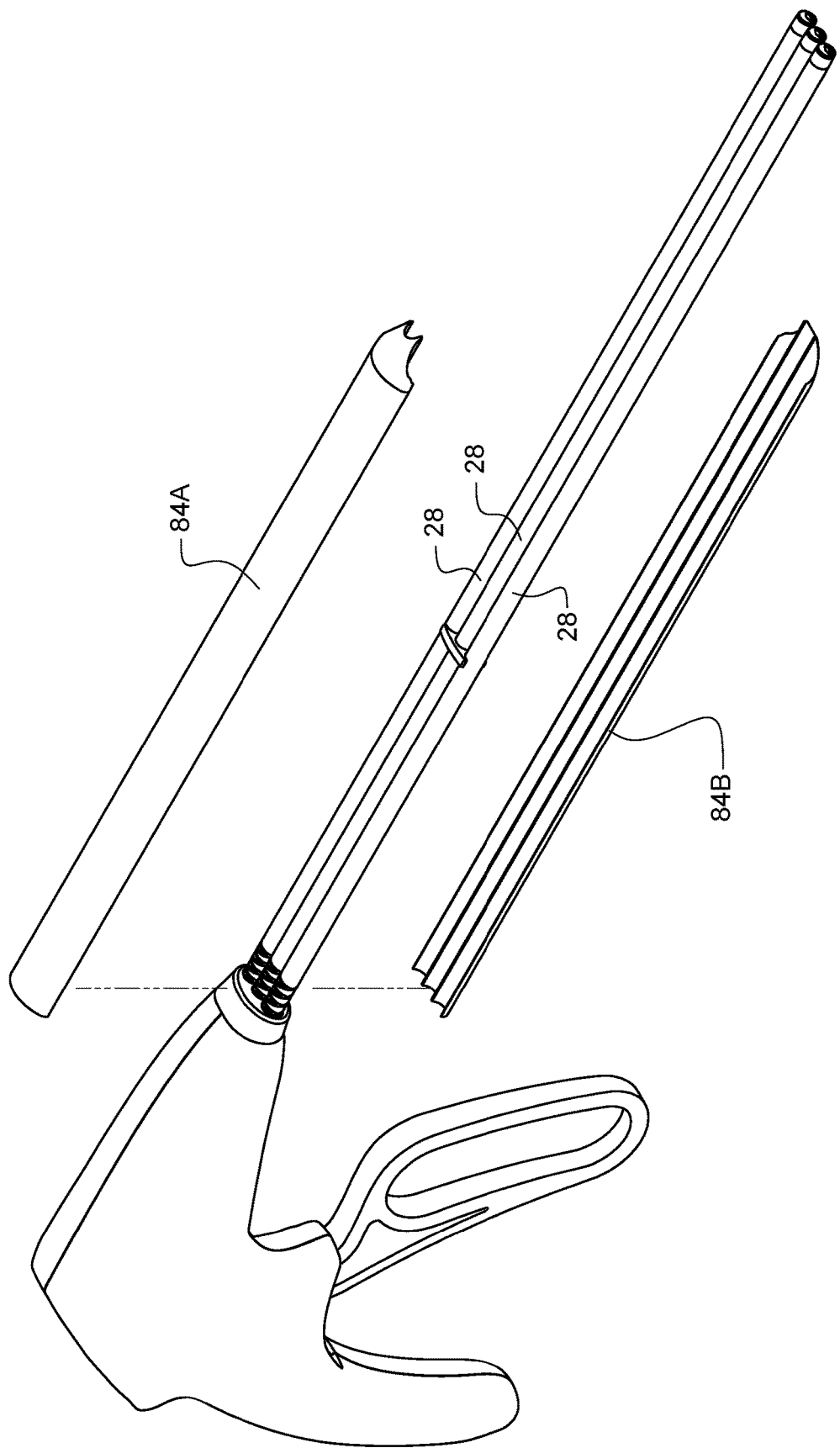
Figure 4G:
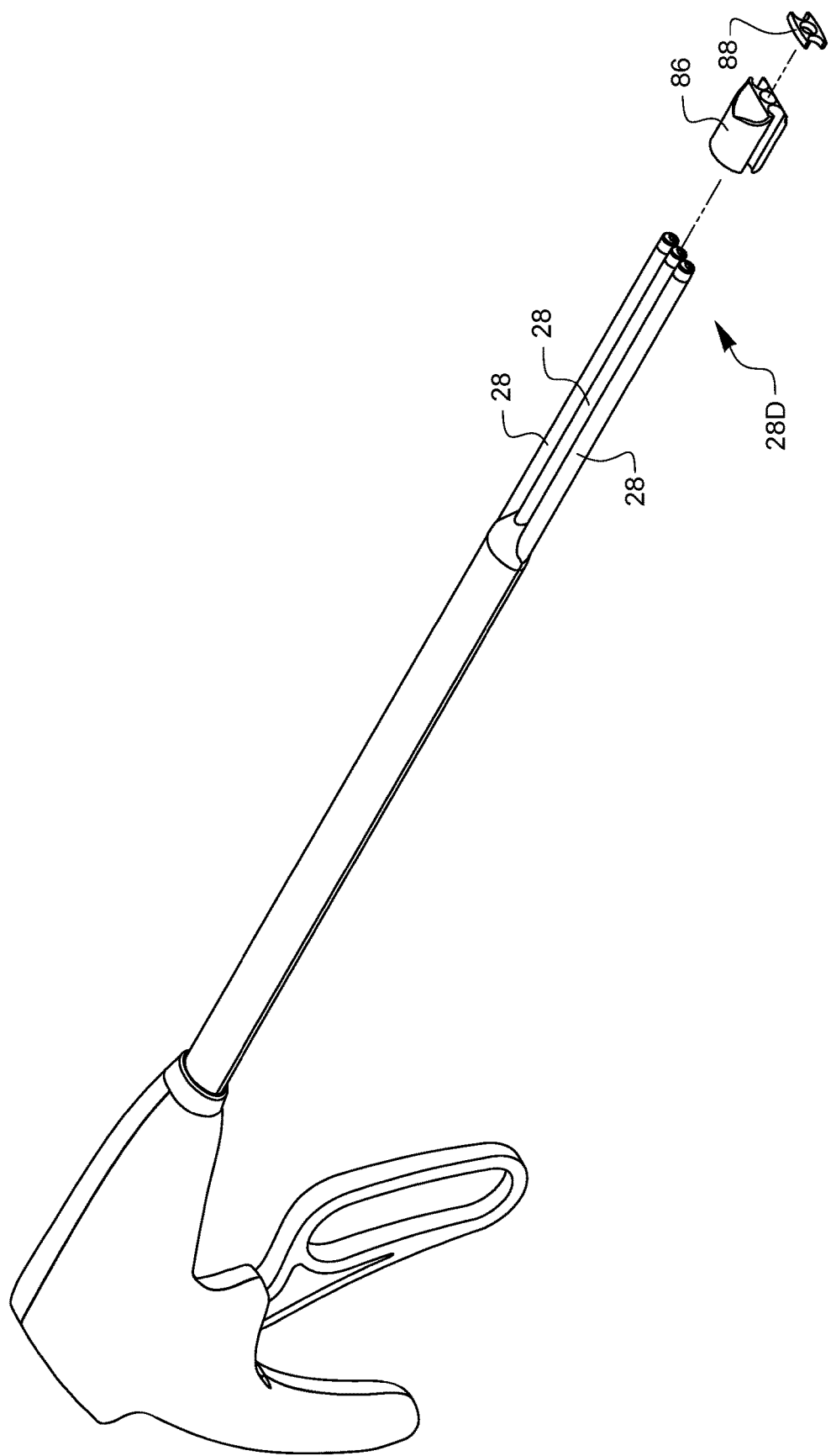
Figure 4H:
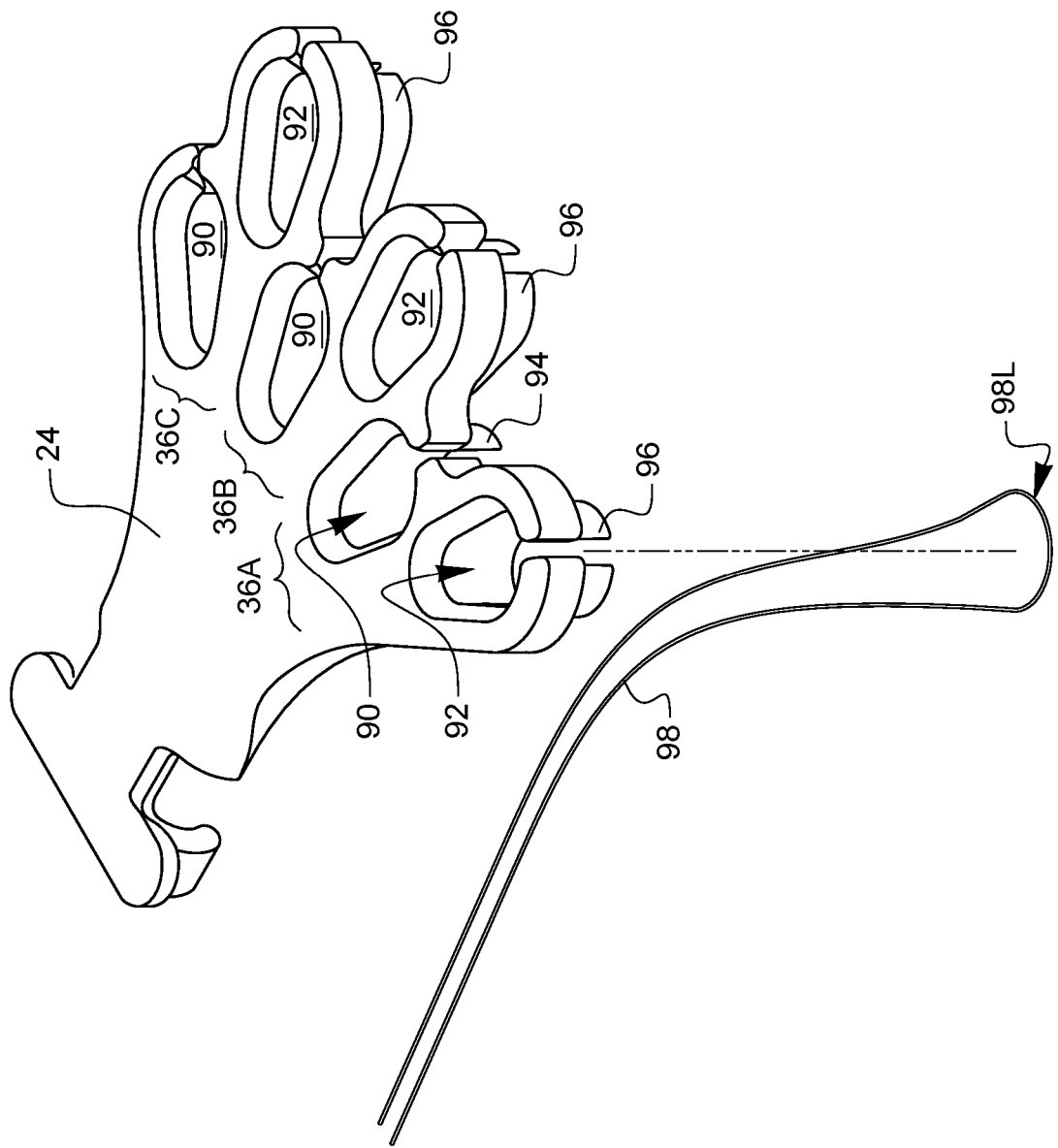
Figure 4J:
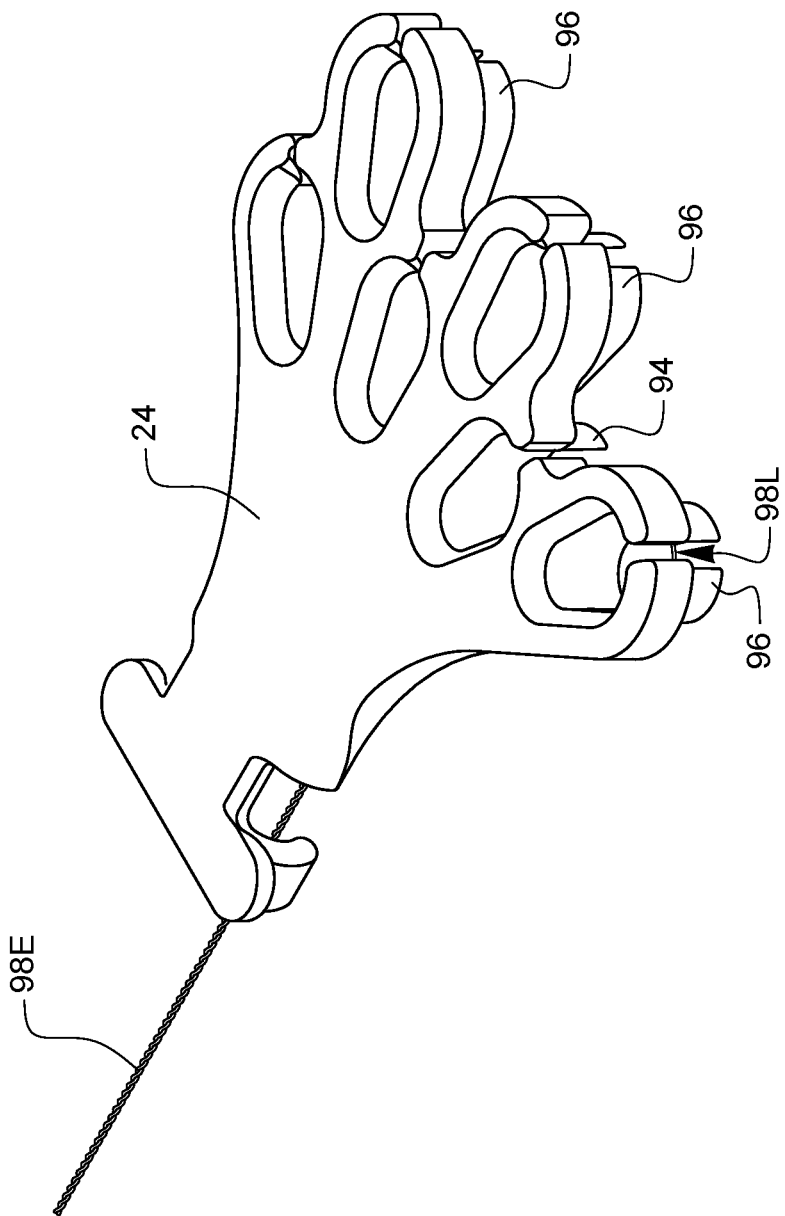
Figure 4L:
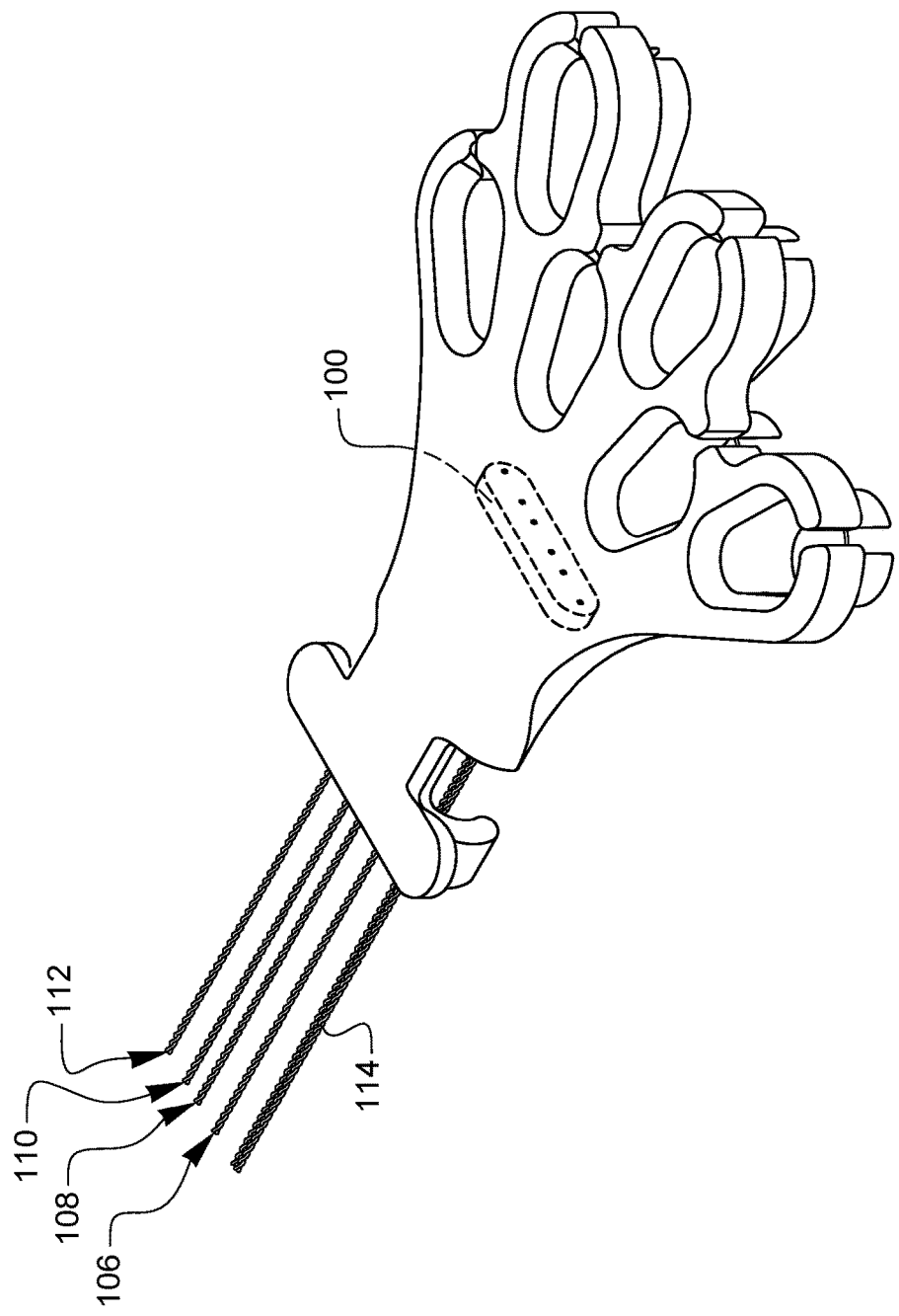
Figure 4M:
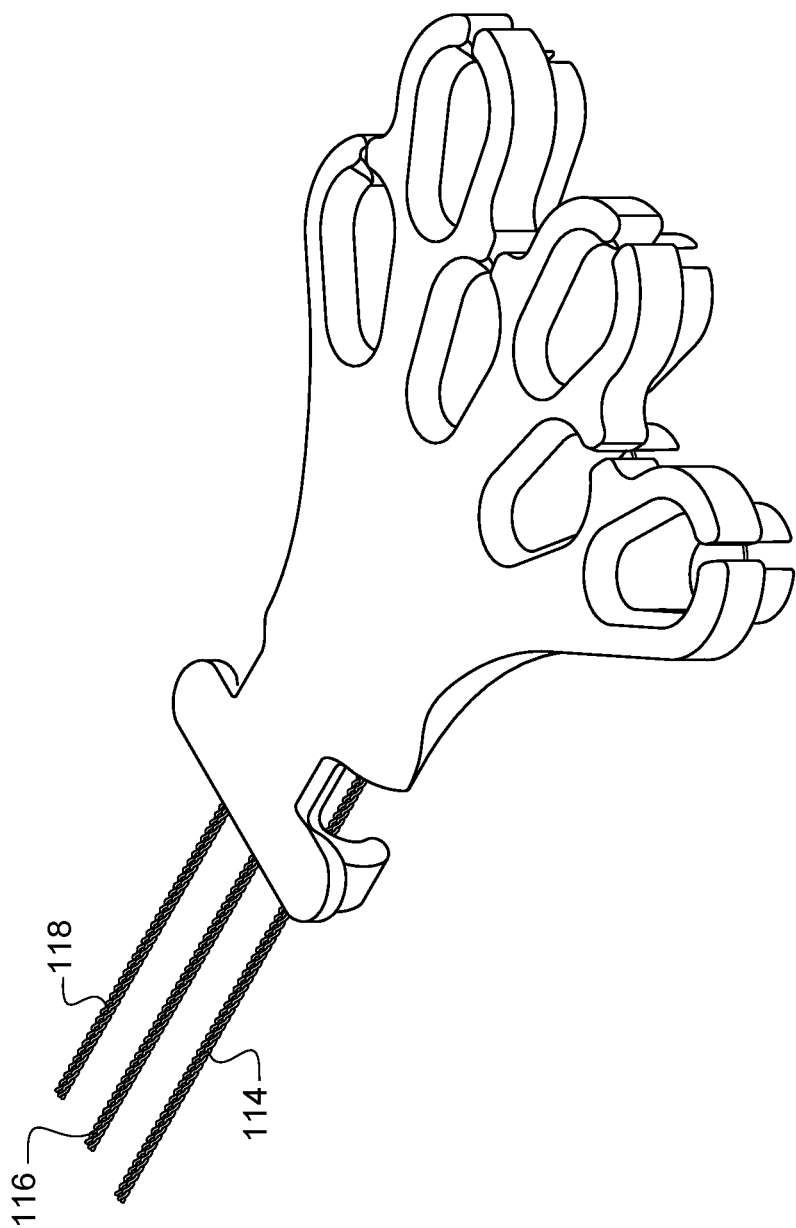
Figure 4N:
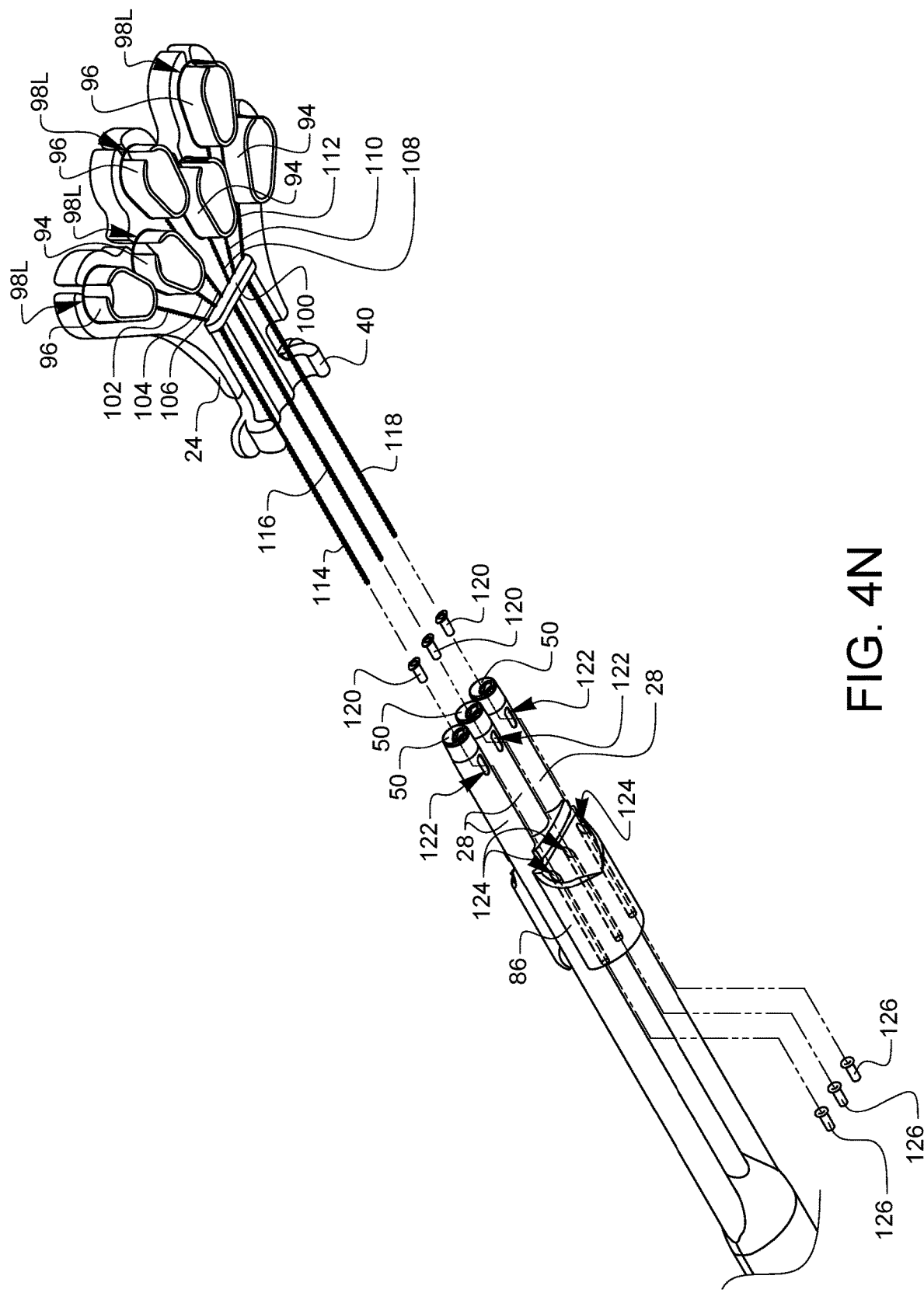
Figure 4P:
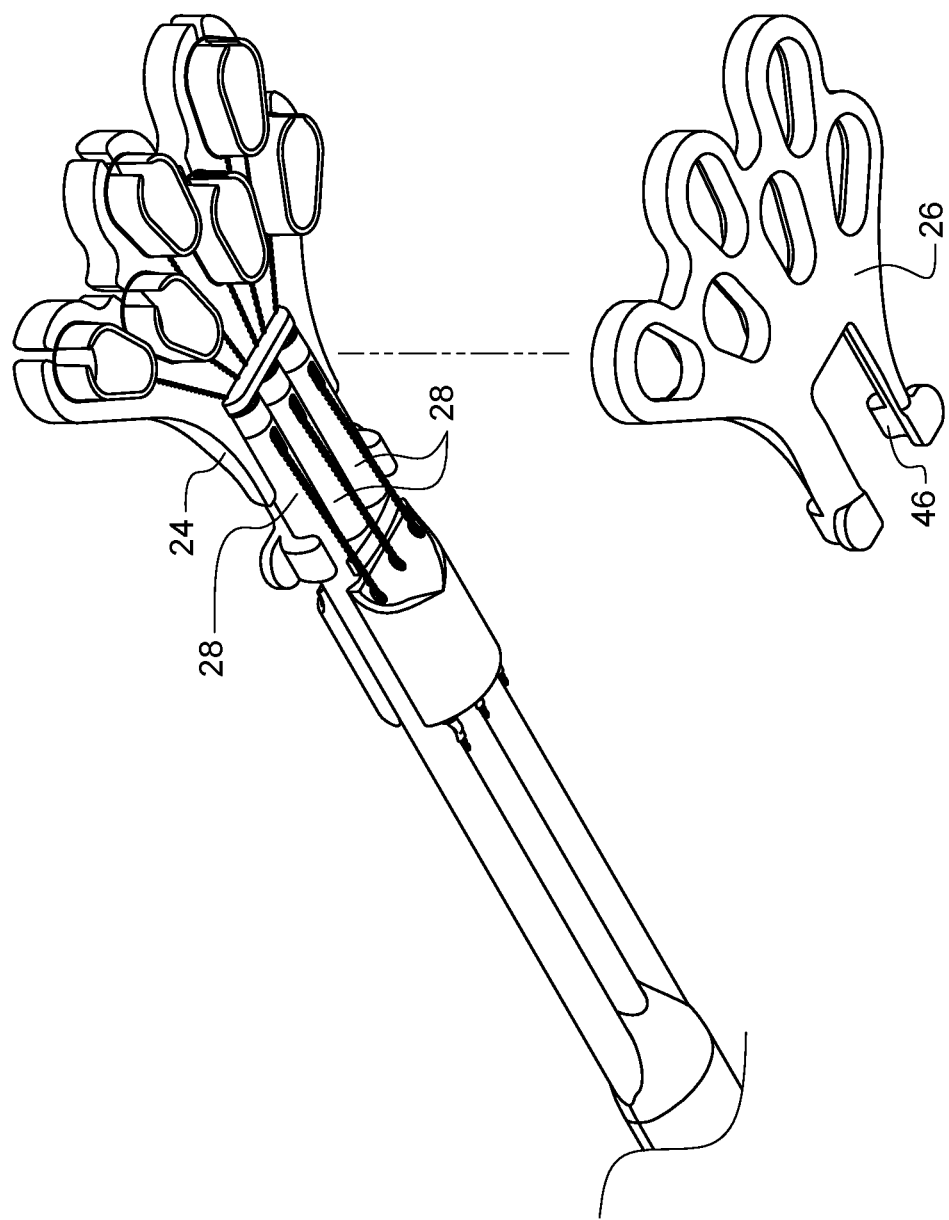

FIGS. 4A-4P are a series of exploded views which illustrate the assembly of one embodiment of a crimping instrument having a loading tool. Note that there are no FIGS. 4I and 4O to avoid possible confusion with similar looking numbers.

As shown in FIG. 4A, a plurality of shafts 28 are coupled to a shaft spacer 48 at the proximal end 28P of the shafts 28. A receiving face 50 is placed into the distal end 28D of the shafts 28. Coupled to each receiving face 50 is a hammer 52 and an anvil 54.

As shown in FIG. 4B, a plurality of pushers 56 are coupled at a proximal end 56P to a drive link 58. The distal end 56D of each pusher 56 has a wedge tip 60 which will ultimately ride against corresponding hammers 52 when the device is assembled and used. In this embodiment, cutting blades 62 are also coupled to the distal end 56D of each pusher 56.

As shown in FIG. 4C, the pusher assembly 56A of FIG. 4B is inserted into the proximal end 28P of the shaft assembly 28A from FIG. 4A.

As shown in FIG. 4D, a different shaft spacer 64 is placed over the distal end 28D of the shafts 28. The drive link 58 coupled to the pushers 56 is further coupled to a receiver 66 in the lever 32, while a lever axle 68 is placed into a boss 70 of a first housing half 72. The first housing half 72 also engages the shaft spacer 48.

As shown in FIG. 4E, a biasing element 74 (in this example, a spring) is connected between a post 76 and the lever 32 in order to bias the lever 32 towards a stop 78 on the housing 72. A second housing half 80 is coupled to the first housing half 72 and has a comparable boss (not visible in this view) to engage the other axle 82 on the lever 32.

As shown in FIG. 4F, in this embodiment, a shaft stabilizer comprising upper and lower stabilizer components 84A, 84B is coupled around a portion of the exposed shafts 28.

As shown in FIG. 4G, a slideable handle 86 is slid over the distal end 28D of the shafts 28, along with another shaft spacer 88.

A target cover 24 is shown in FIG. 4H. It is helpful to note that in this embodiment, there are three pairs of target cover suture openings 36A, 36B, and 36C. Each pair of target cover suture openings 36A, 36B, 36C has proximal suture opening 90 and a distal suture opening 92. Each suture opening, as described previously with regard to FIGS. 2A-2F has a corresponding snare guide, and therefore the proximal suture openings 90 have corresponding proximal snare guides 94 (only one of which is easily viewable in FIG. 4H). Likewise, the distal suture openings 92 have corresponding distal snare guides 96. As shown in FIG. 4H, a snare wire 98 is wrapped around the distal snare guide 96 of the first pair of snare guides to form a snare loop 98L. As shown in FIG. 4J, the ends 98E of the snare wire 98 are twisted together to complete the snare loop 98L. This process of forming snare loops around each of the snare guides 96, 94 is repeated, resulting (in this embodiment) in six snare loops and six twisted snare wire ends 98E as shown in FIG. 4K. Each of the twisted wire ends 98E is passed through a pledget 100. The first twisted ends 102 are coupled to the distal snare loop in the first pair of snare loops. The second twisted ends 104 are coupled to the proximal snare loop in the first pair of snare loops. The third twisted ends 106 are coupled to the distal snare loop in the second pair of snare loops. The fourth twisted ends 108 are coupled to the proximal snare loop in the second pair of snare loops. The fifth twisted ends 110 are coupled to the distal snare loop in the third pair of snare loops. The sixth twisted ends 112 are coupled to the proximal snare loop in the third pair of snare loops.

As shown in FIG. 4L, the first and second twisted ends 102, 104 are further twisted together proximal to the pledget 100 into a first pair snare wire 114. As shown in FIG. 4M, the third and fourth twisted ends 106, 108 are further twisted together proximal to the pledget 100 into a second pair snare wire 116. Similarly, the fifth and sixth twisted ends 110, 112 are further twisted together proximal to the pledget 100 into a third pair snare wire 118.

As shown in FIG. 4N, the twisted snare wires 114, 116, 118 are then passed through respective crimpable fasteners 120. The crimpable fasteners 120 are seated in corresponding receiving faces 50, while the twisted snare wires 114, 116, and 118 are also passed out of corresponding slots 122 and into channels 124 of the sliding handle 86. The twisted snare wires 114, 116, 118 are then coupled to the sliding handle 86 in this embodiment with fasteners 126. In this way, the handle 86 is coupled to the plurality of snare loops such than movement of the handle (in this example, in a proximal direction) will draw the snare loops through the suture fasteners 120. The coupling latch 40 of the target cover 24 is also coupled around the shafts 28 to hold the target cover 24 in place.

As shown in FIG. 4P, the target tray 26 is aligned under the target cover 24 in order to help prevent snare loops from falling off the snare loop guides prematurely. The coupling latch 46 of the target tray 26 is coupled around the shafts 28 to hold the target tray in place.

Figure 5A:
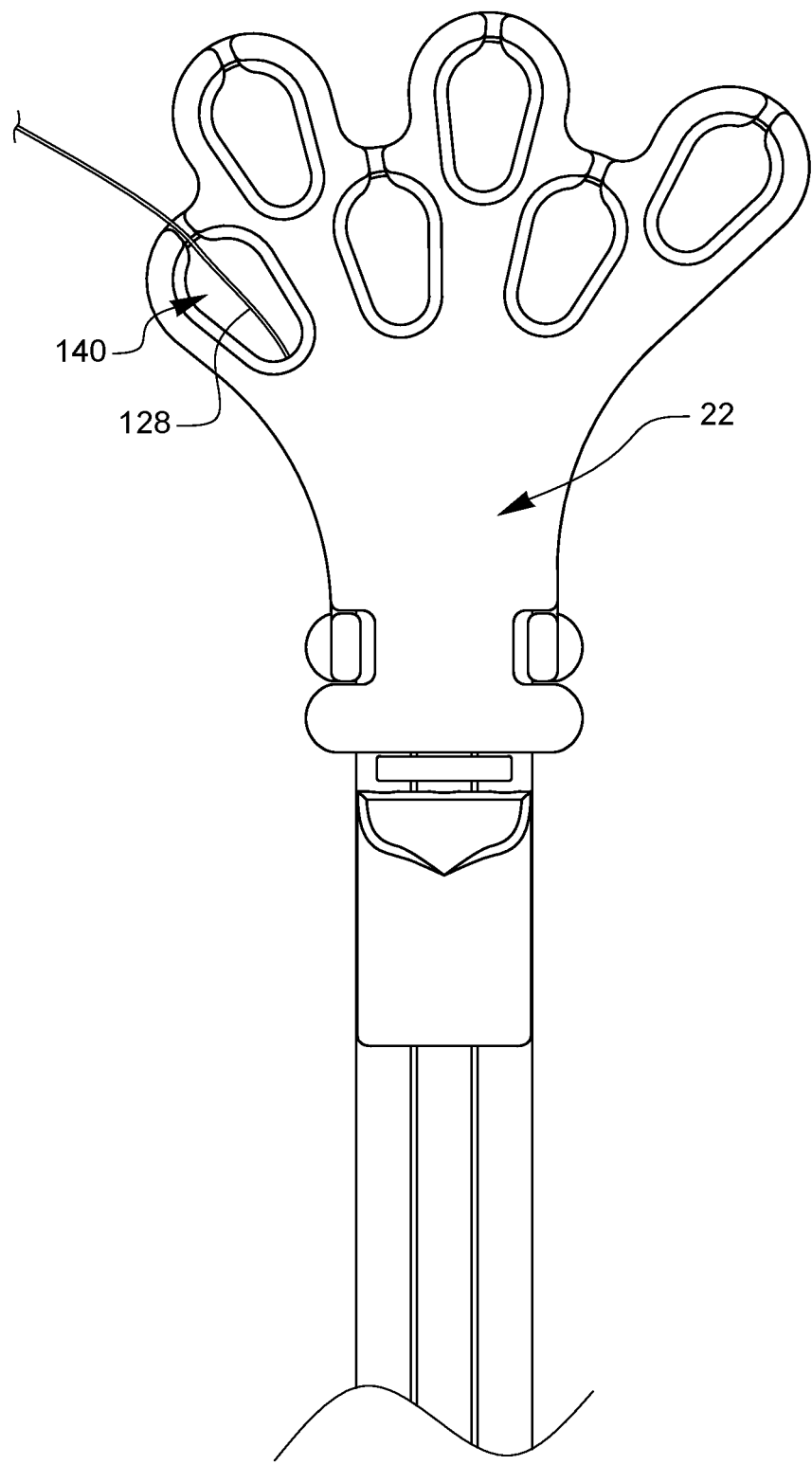
FIGS. 5A-5H illustrate one embodiment of a usage example where sutures are loaded into a crimping instrument with an embodiment of a loading tool.
Figure 5B:
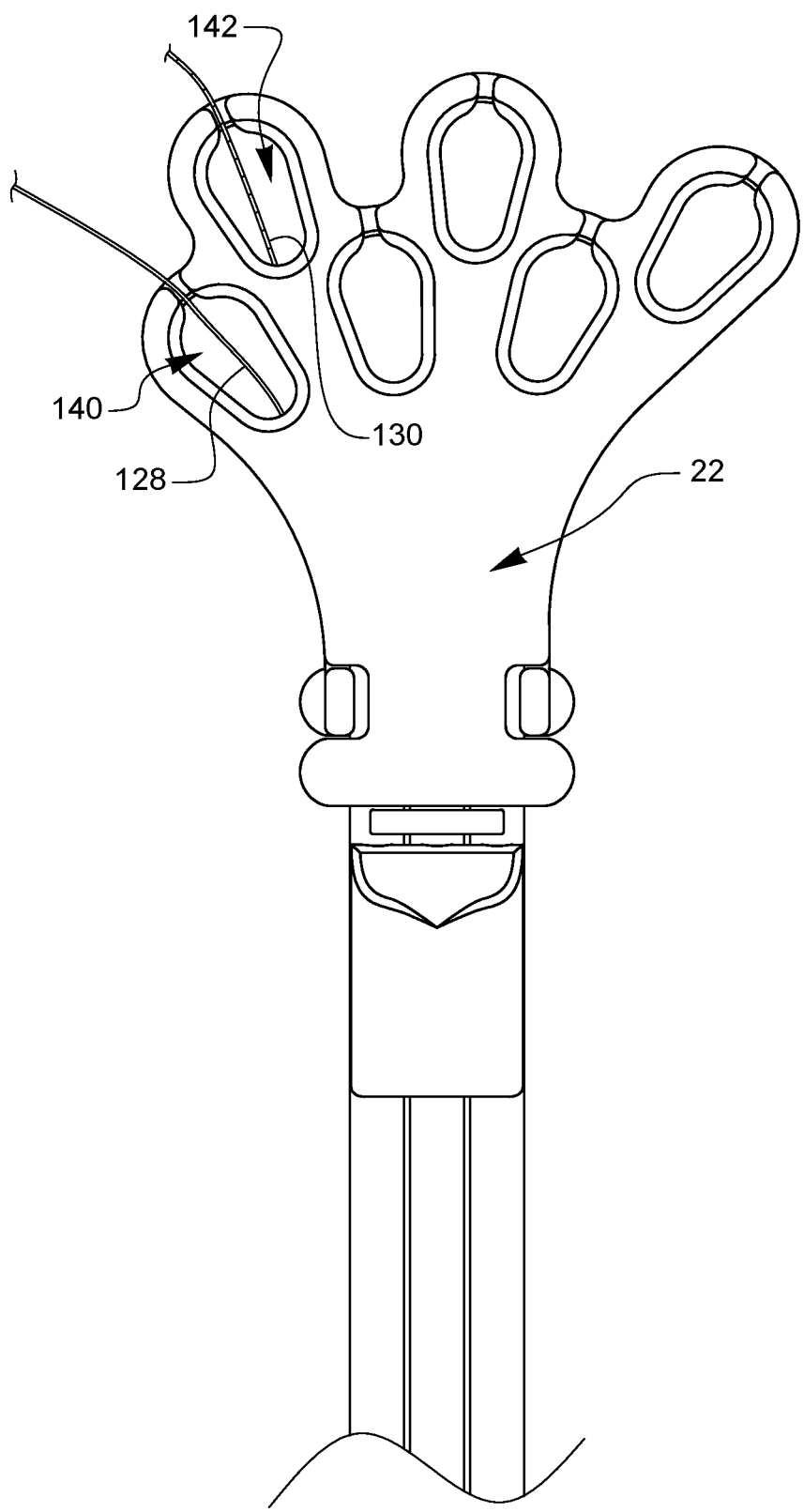
Figure 5C:
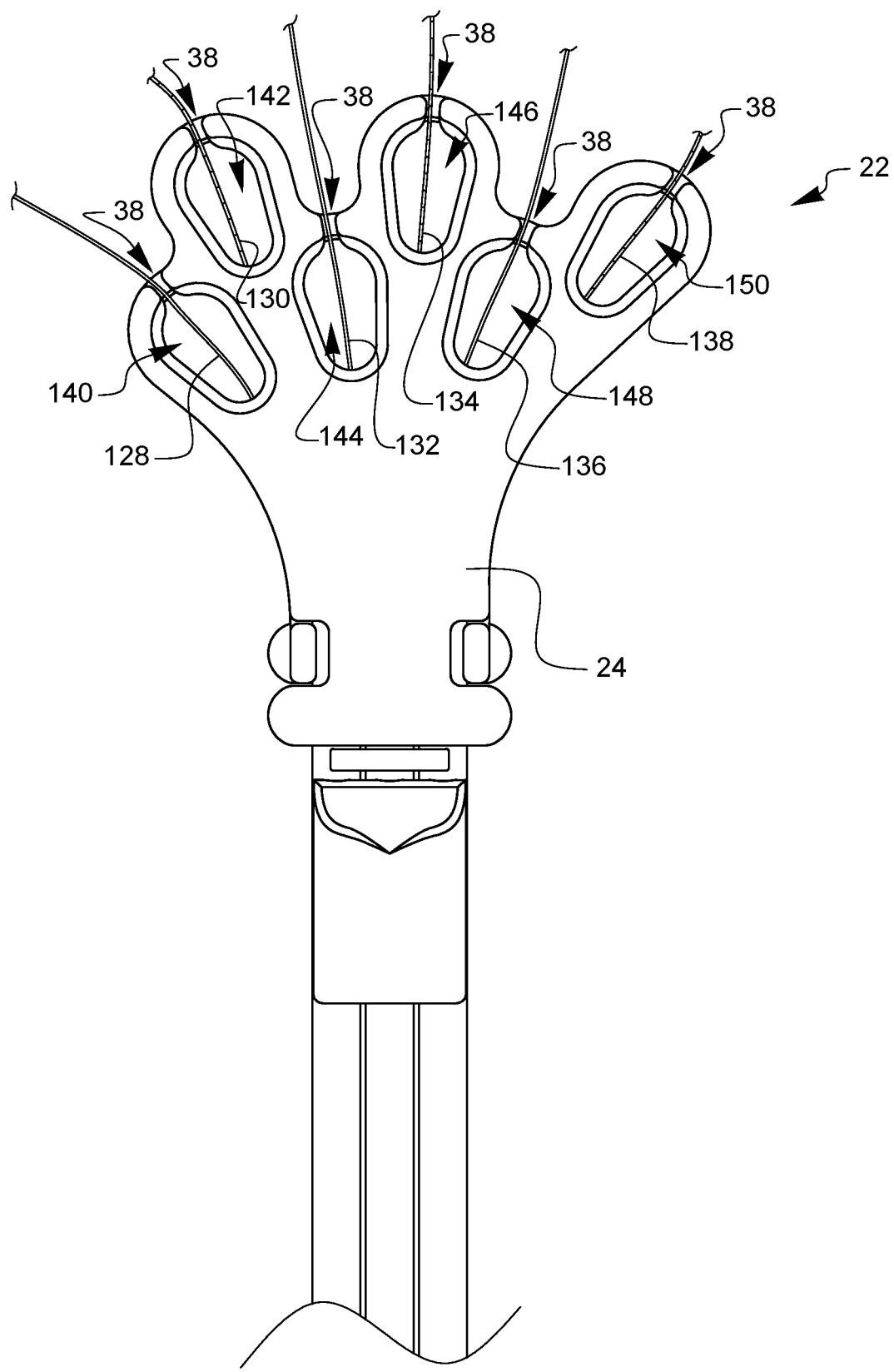
Figure 5D:
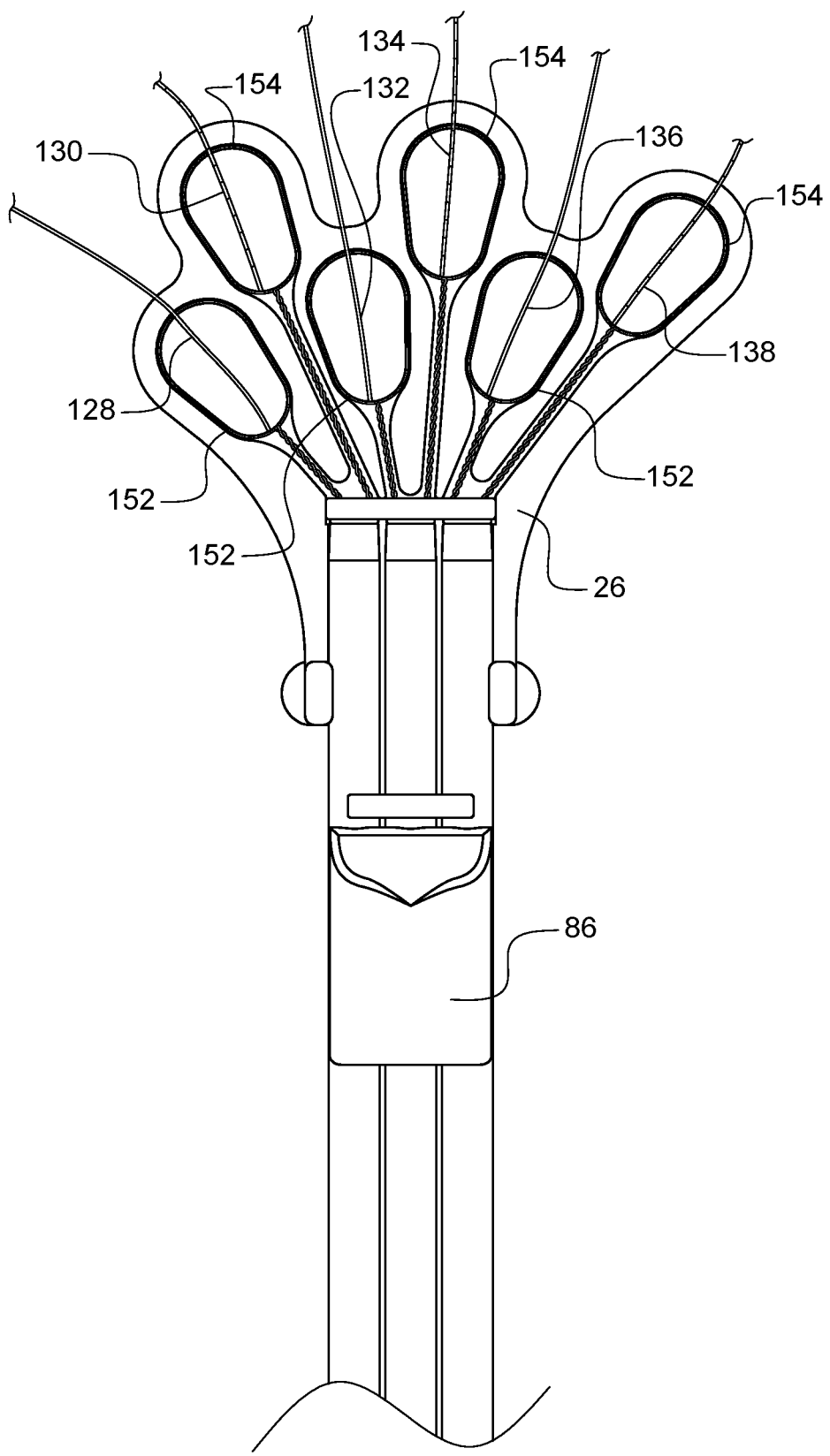
Figure 5E:
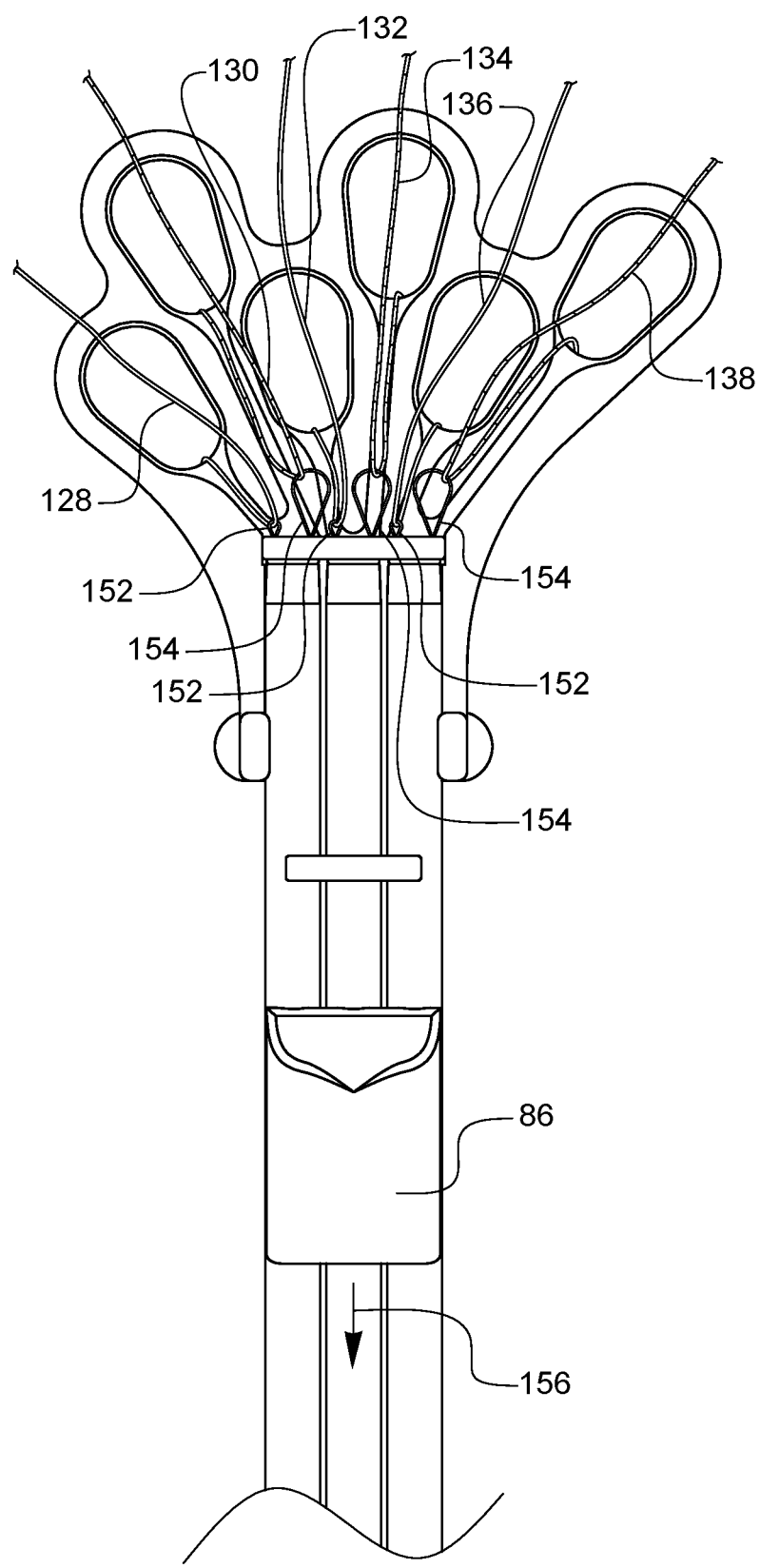

FIGS. 5A-5H illustrate one embodiment of a usage example where sutures are loaded into a crimping instrument with an embodiment of a loading tool 22. As illustrated in FIGS. 5A-5C, a first suture end 128, a second suture end 130, a third suture end 132, a fourth suture end 134, a fifth suture end 136, and a sixth suture end 138 are each placed through respective suture openings 140, 142, 144, 146, 148, and 150. The target cover 24 is then removed, as depicted by the exposed target tray 26 and the exposed proximal snare loops 152 and the exposed distal snare loops 154 as shown in FIG. 5D. This is possible because the suture clearance slots 38 (visible in FIG. 5C) can pass over the sutures 128, 130, 132, 134, 136, and 138. As shown in FIG. 5E, the handle 86 is moved in a proximal direction 156, which pulls the proximal snare loops 152 and the distal snare loops 154 towards the suture fastener (not visible in this view) held in the distal end of the device. As the snare loops 152, 154 are pulled through the fasteners by the movement of the handle 86, so too are the snared sutures 128, 130, 132, 134, 136, and 138 also pulled through the fasteners. Embodiments like this, where the proximal and distal snare loops are staggered, allow the different sutures to be pulled through the suture fastener at different times, thereby enabling the size of the crimpable fastener to be smaller.

Figure 5F:
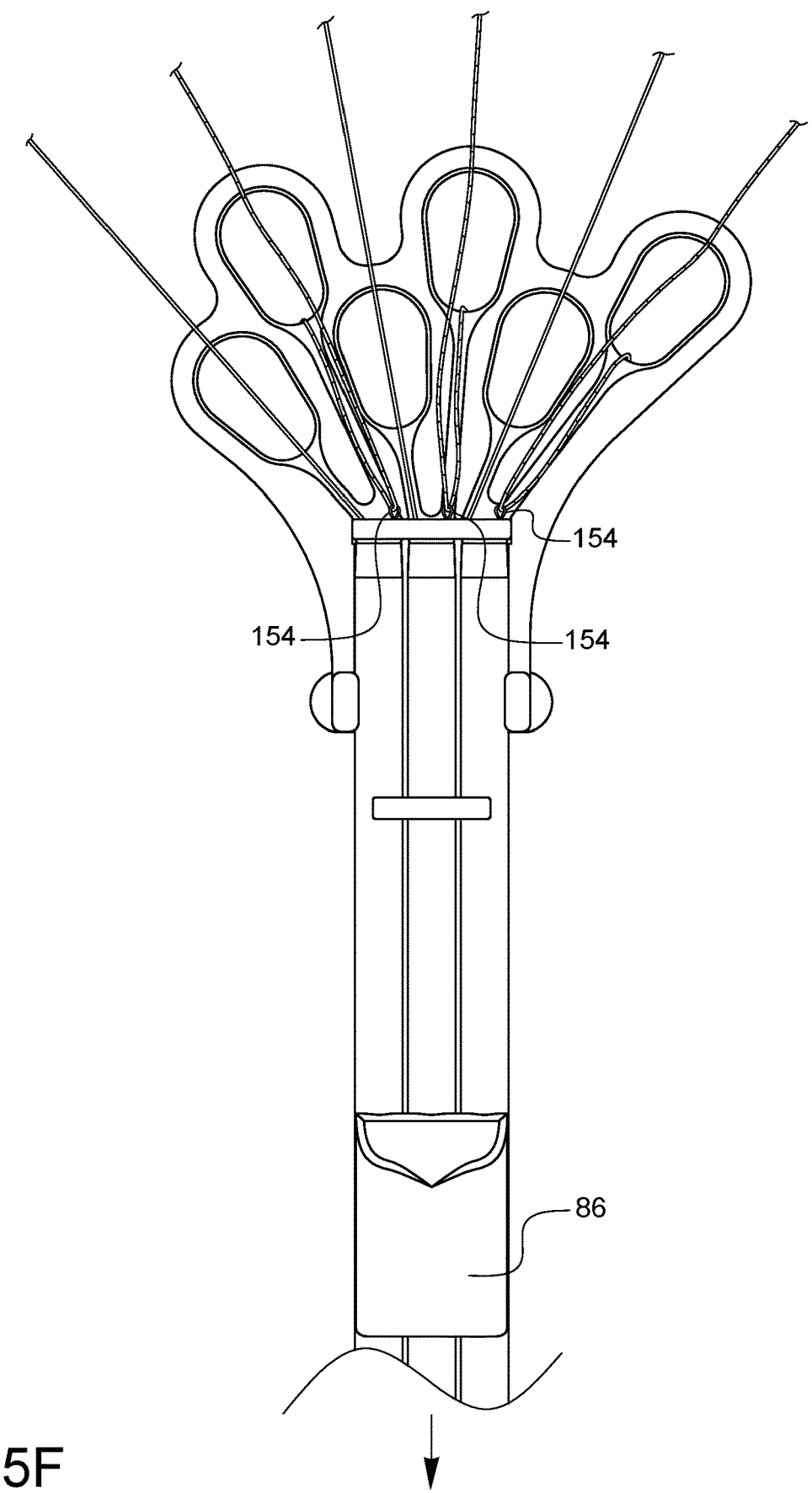

FIG. 5F shows the handle 86 having been moved more proximally, whereby the proximal snare loops have already been pulled through the suture fasteners, and the distal snare loops 154 are going through the suture fasteners.

Figure 5G:
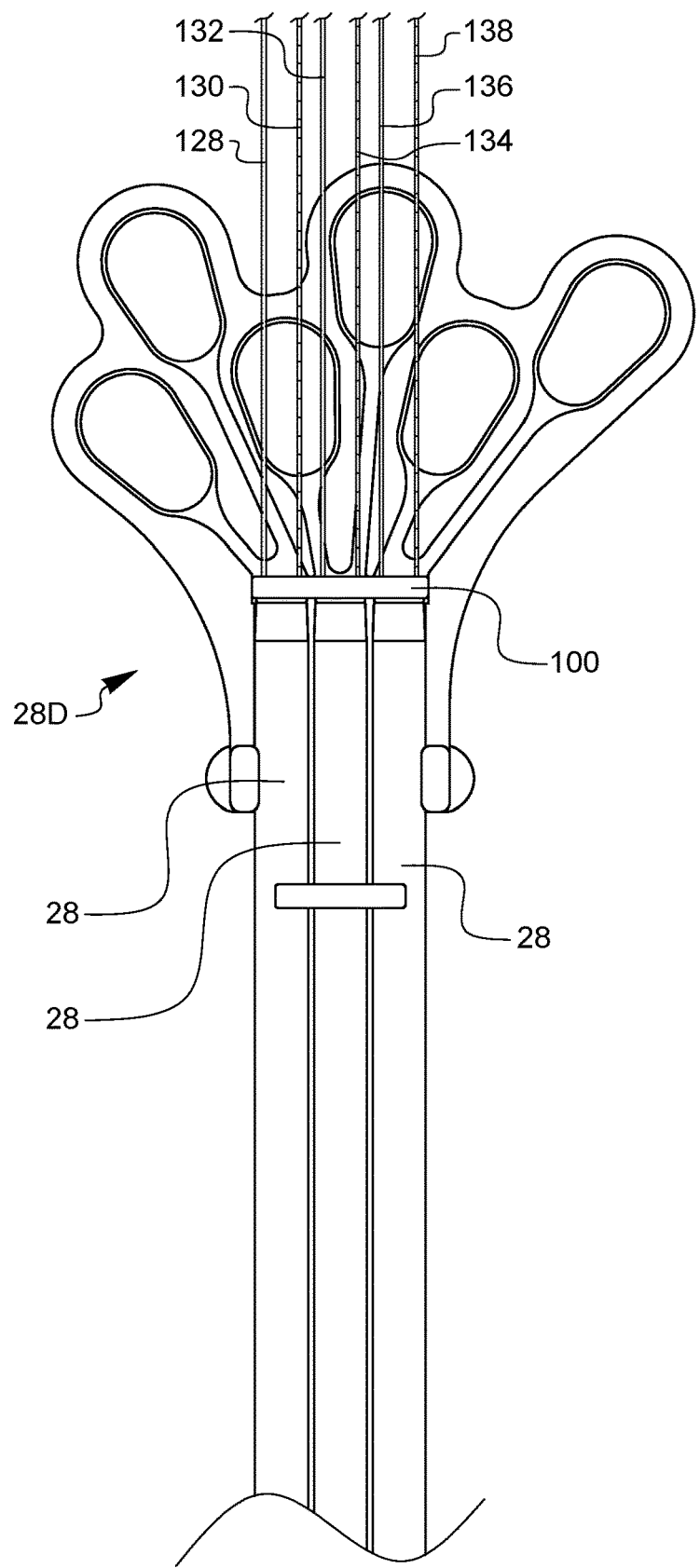
Figure 5H:
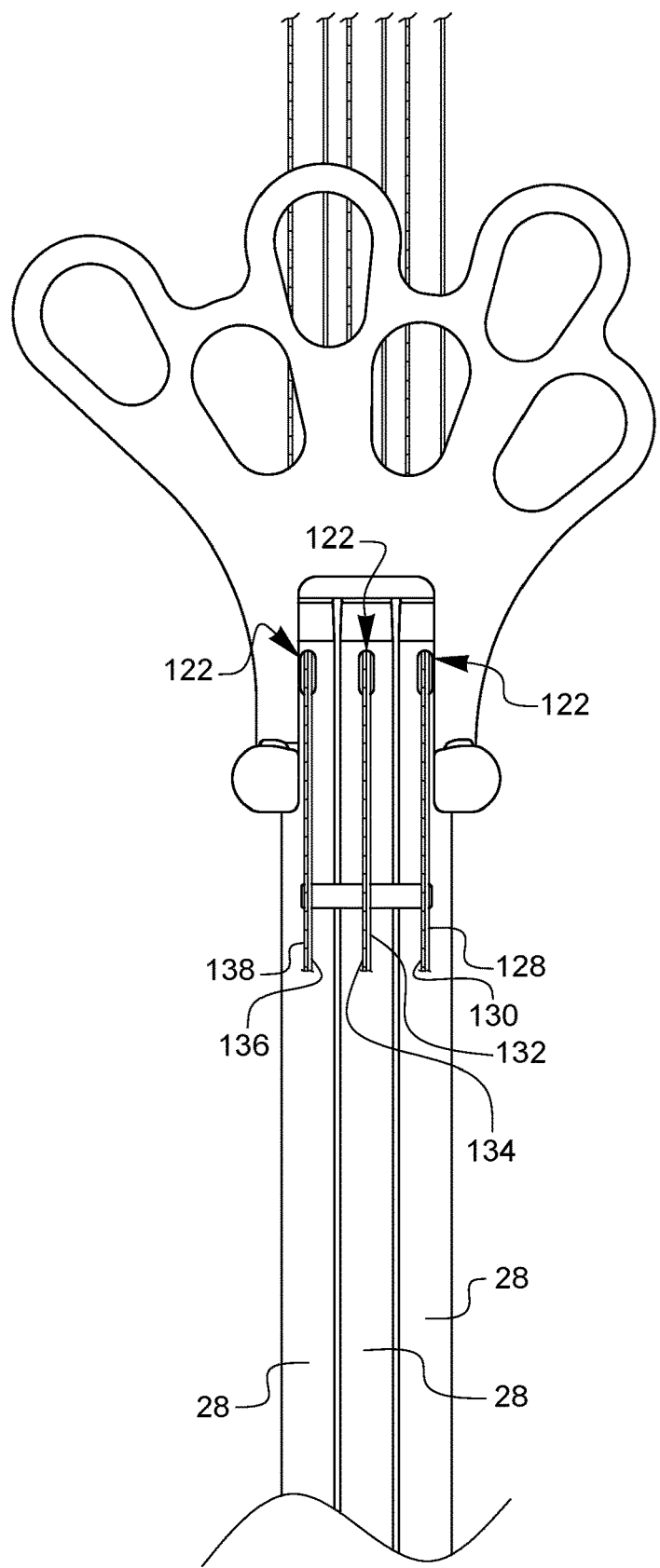

In FIG. 5G, the sutures 128, 130, 132, 134, 136, 138 have been fully snared through not only the pledget 100 but also through the three suture fasteners. Although the suture fasteners are not visible in this view, there is one suture fastener in the distal end 28D of each shaft 28. The sutures 128 and 130 are passed through the first suture fastener. The sutures 132 and 134 are passed through the second suture fastener, and the sutures 136 and 138 are passed through the third suture fastener. In FIG. 5H, the device has been flipped over to see the suture pairs 128, 130 and 132, 134 and 136, 138 exiting the slots 122 on the underside of the shafts 28. At this point, the sutures may be tensioned as desired, and the device lever may be squeezed, causing the pusher to move distally, thereby causing the wedge tip to compress the hammer towards the anvil, crimping the suture fastener therebetween so that it secures the sutures within the suture fastener. The cutting blade attached to the pusher can also cut the suture ends exiting the slots 122.

Figure 6A:
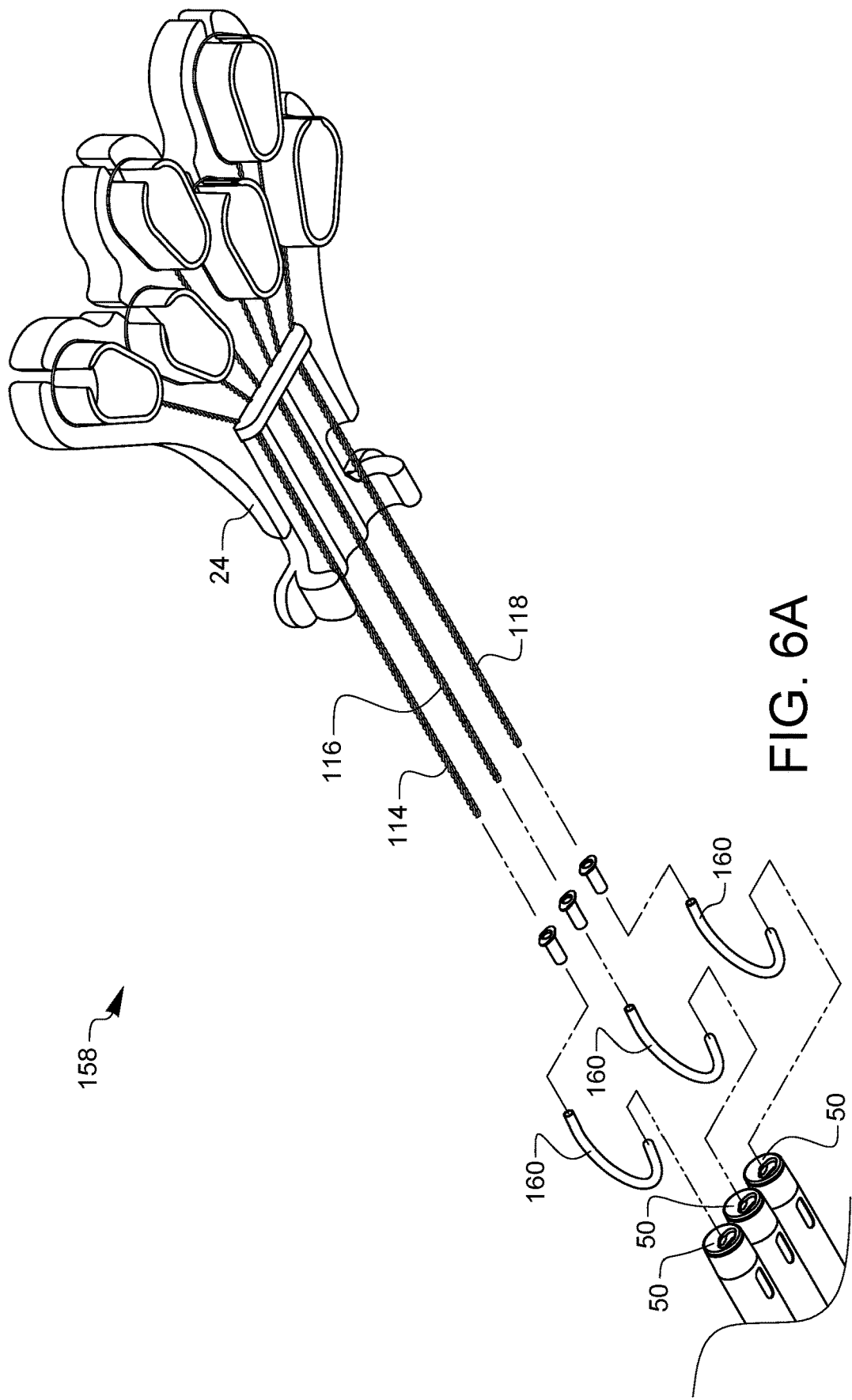
Figure 6C:
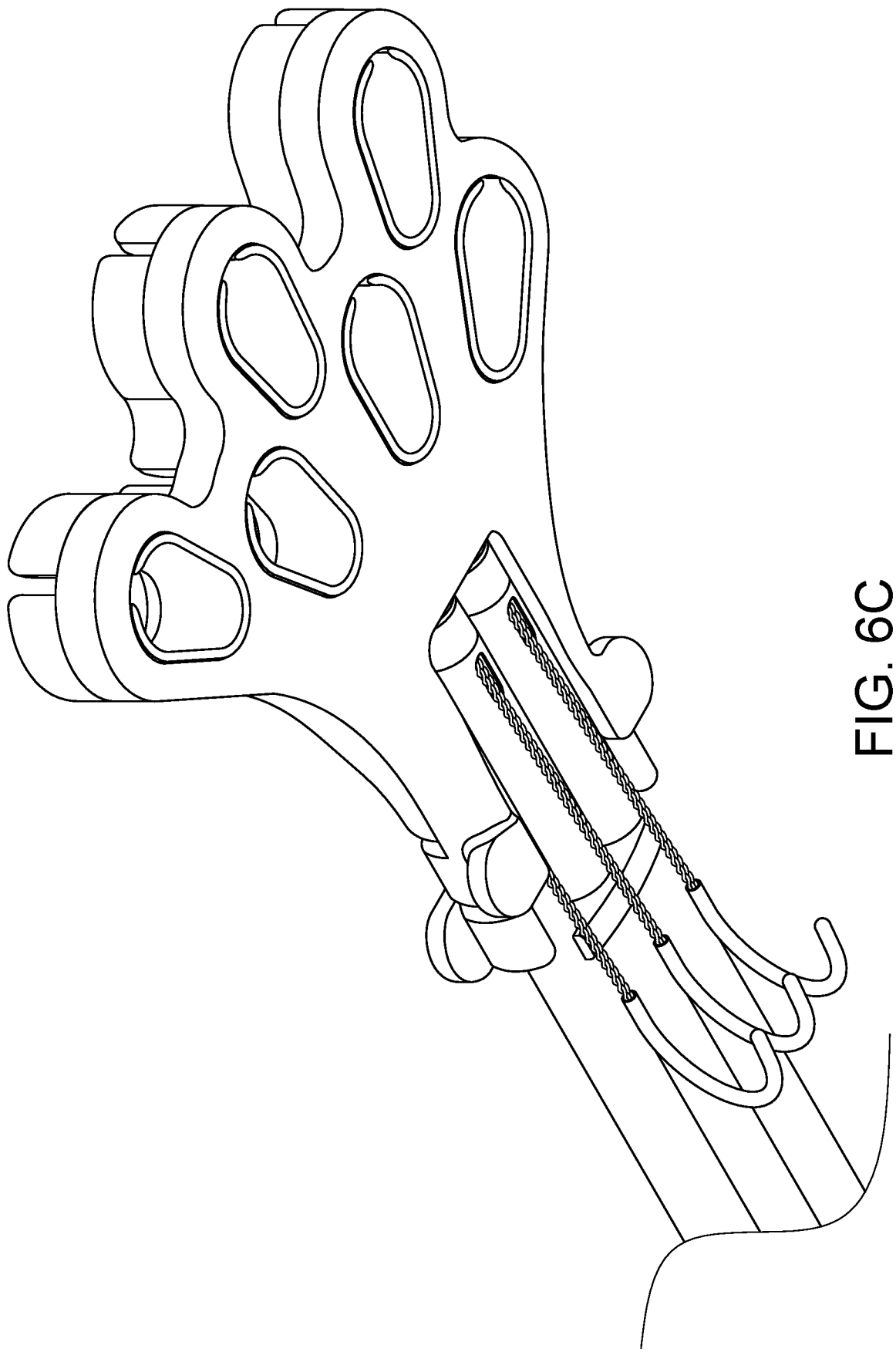

FIGS. 6A-6C are partially exploded views illustrating another embodiment of a loading tool 158 for a surgical crimping instrument. This embodiment is similar to previous embodiments, except for the handle. In this embodiment, there are three separate handles 160 coupled to respective twisted snare wires 114, 116, and 118. These separate handles 160 are more easily loaded by an end user, one in each receiving face 50, for situations where the instrument is desired to be reloaded or user loaded. As illustrated in FIG. 6B, after the handles have been loaded into the instrument, the target cover 24 can be snapped onto the instrument, and the target tray 26 can be snapped over the instrument to cover the target cover 24. FIG. 6C shows the end result.

Figure 7:
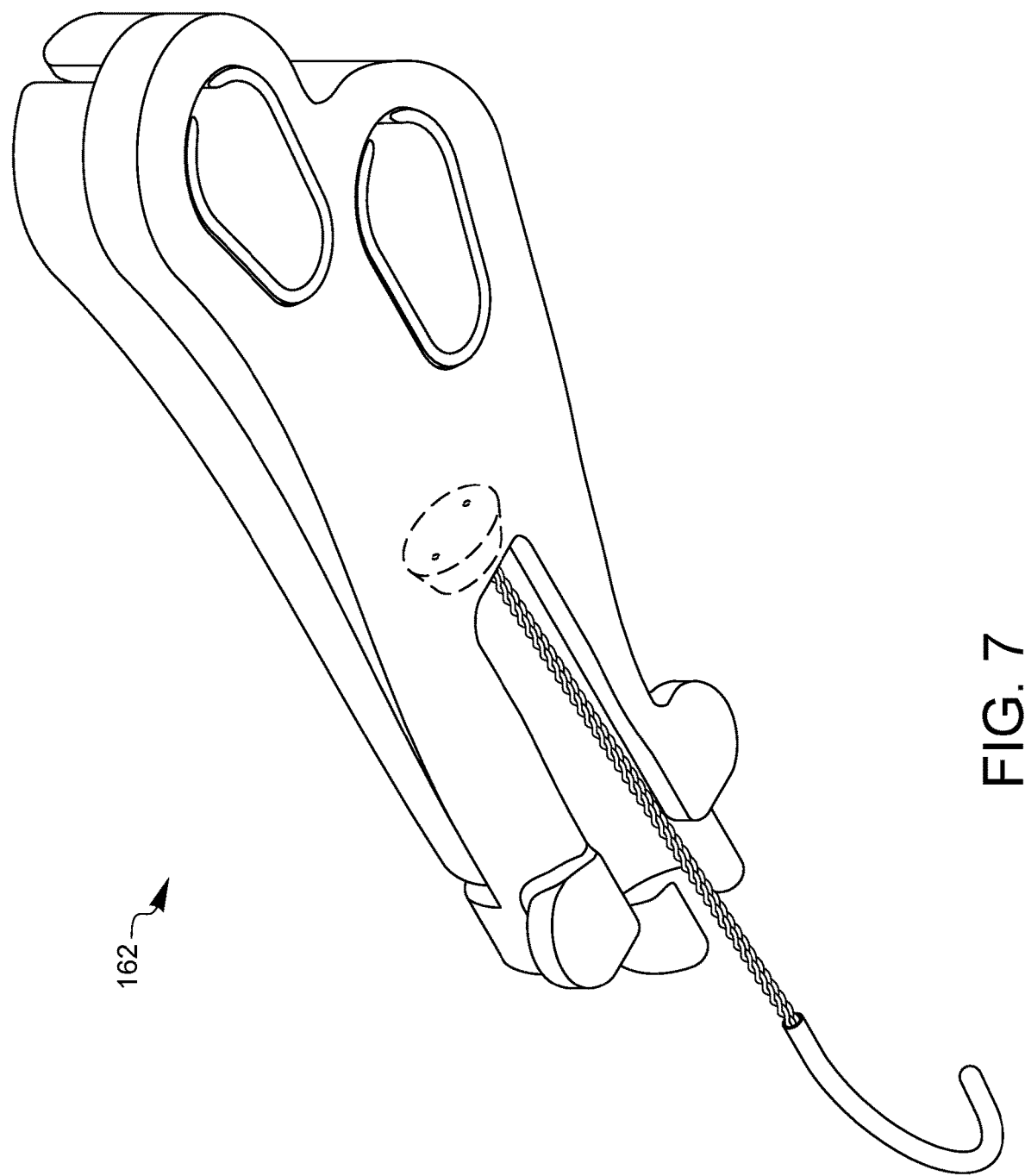
FIG. 7 illustrates a further embodiment of a loading tool for a surgical crimping instrument.

FIG. 7 illustrates a further embodiment of a loading tool 162 for a surgical crimping instrument. The previous embodiments had three pairs of snare loops. This embodiment has one pair of snare loops. Other embodiments may have just one snare loop or an odd number of snare loops. Still other embodiments may have snare loops which are each substantially equidistant from the suture fasteners so that there is not a distinguishable difference between proximal vs distal snare loops.

Various advantages of a crimping instrument and loading tool therefor have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An instrument for crimping one or more suture fasteners to one or more corresponding surgical sutures, the instrument comprising:
   at least one shaft;
   one or more receiving faces, each configured to receive one of the one or more suture fasteners;
   one or more anvils, each of the one or more anvils corresponding to one of the one or more receiving faces;
   one or more hammers, each of the one or more hammers corresponding to one of the one or more anvils and moveable relative to its corresponding anvil for crimping the one or more suture fasteners therebetween and received in the one or more receiving faces;
  one or more pushers moveable in a direction substantially parallel to a longitudinal axis of the at least one shaft and configured to engage at least one of the hammer and the anvil for urging the hammer and the anvil together; and
  a loading tool, comprising:
    a target cover defining one or more snare guides;
    a target tray coupled to the target cover;
    one or more suture fasteners, each of the one or more suture fasteners located within a corresponding one of the one or more receiving faces of the instrument;
    one or more snare loops, each wrapped around a corresponding one of the one or more snare guides; and
    at least one handle coupled to the one or more snare loops such that movement of the at least one handle draws the one or more snare loops to which it is coupled through one or more of the suture fasteners.

2. The instrument of claim 1, wherein the one or more snare guides comprise at least one pair of snare guides.

3. The instrument of claim 2, wherein each of the at least one pair of snare guides comprises a proximal snare guide and a distal snare guide.

4. The instrument of claim 3, wherein each of the one or more snare loops comprise at least one pair of snare loops, comprising:
  a proximal snare loop formed around the proximal snare guide of the of the at least one pair of snare guides; and
  a distal snare loop formed around the distal snare guide of the at least one pair of snare guides.

5. The instrument of claim 4, wherein each of the at least one pair of snare loops is coupled to the at least one handle through a corresponding one of the one or more suture fasteners.

6. The instrument of claim 5, further comprising a pledget through which the one or more snare loops are also coupled to the at least one handle.

7. The instrument of claim 1, wherein the target cover defines one or more target cover suture openings, each of which lies at least partially within a corresponding one of the one or more snare guides.

8. The instrument of claim 7, wherein the target tray defines one or more target tray suture openings, each of which corresponds to one of the one or more target cover suture openings.

9. The instrument of claim 7, wherein the target cover further defines a suture clearance slot coupled to each of the one or more target cover suture openings.

10. The instrument of claim 1, wherein the at least one handle is slideable on the at least one shaft.

11. An instrument for crimping each of two or more suture fasteners, the instrument comprising:
  a housing;
  two or more shafts coupled to the housing, each of the two or more shafts extending along a longitudinal axis from a proximal end to a distal end, and each of the two or more shafts having one or more interior surfaces that define an interior portion;
  two or more receiving faces, each of the two or more receiving faces being at least partially received into a portion of the interior portion disposed at or adjacent to the distal end of a corresponding one of the two or more shafts, each of the two or more receiving faces being coupled to a hammer and an anvil, and each of the two or more receiving faces being configured to receive a corresponding one of the two or more suture fasteners between the hammer and the anvil;
  two or more pushers, each of the two or more pushers extending along a longitudinal axis from a proximal end to a distal end and each of the two or more pushers at least partially disposed in the interior portion of a corresponding one of the two or more shafts, each of the two or more pushers moveable in a direction substantially parallel to the longitudinal axis of the corresponding one of the two or more shafts from a disengaged position to an engaged position in which the distal end is configured to engage at least one of the hammer and the anvil of a corresponding one of the two or more receiving faces for urging the hammer and the anvil together to crimp the corresponding one of the two or more suture fasteners; and
  a lever movably coupled to the housing such that the lever is displaceable between a first position and a second position, wherein a portion of the lever is coupled to the proximal end of each of the two or more pushers such that when the lever displaced from the first position to the second position, each of the two or more pushers are displaced from the disengaged position to the engaged position,
  wherein a portion of suture is configured to be inserted through an aperture of a corresponding one of the two or more suture fasteners such that when the lever is displaced from the first position to the second position, the corresponding one of the two or more suture fasteners is crimped to secure the portion of suture within the aperture of the corresponding one of the two or more suture fasteners.

12. The instrument of claim 11, further comprising a loading tool disposed at or adjacent to the distal end of each of the two or more shafts, the loading tool comprising a target cover comprising:
  two or more suture openings that extend from a top surface to a bottom surface of the target cover, each of the two or more suture openings being defined by a perimeter edge portion; and
  two or more snares guides extending from the bottom surface of the target cover, each of the two or more snares guides comprising a projection that extends along a corresponding one of the perimeter edge portions, wherein each of the two or more snares guides is configured to support a first portion of a snare wire that surrounds each of the two or more snares guides, wherein a second portion of the snare wire is configured to extend through a corresponding one of the two or more suture fasteners, and
  wherein the portion of suture is configured to be inserted into a corresponding one of the two or more suture openings of the target cover and the corresponding snare wire is configured to draw the portion of suture through the aperture of the corresponding one of the two or more suture fasteners.

13. The instrument of claim 12, further comprising a handle that is displacably coupled to each of the two or more shafts such that the handle is displaceable in a direction parallel to the longitudinal axis of each of the two or more shafts, the handle configured to be fixedly coupled to a third portion of the snare wire such that displacement of the handle draws the portion of suture through the corresponding one of the two or more suture fasteners.

14. The instrument of claim 12, the loading tool further comprising a target tray removably coupled to the target cover, the target tray comprising two or more suture openings that extend from a top surface to a bottom surface of the target tray, each of the two or more suture openings being defined by a perimeter edge portion, each of the perimeter edge portions of the target tray being aligned with a corresponding one of the perimeter edge portions of the target cover such that each of the two or more suture openings of the target cover are aligned with a corresponding one of the two or more suture openings of the target tray.

15. The instrument of claim 14, wherein a bottom portion of each of the two or more snares guides contacts or is adjacent to a portion of the top surface of the target tray to maintain the first portion of the snare wire around a corresponding one of the two or more snares guides.

16. The instrument of claim 12, wherein the perimeter edge portions each of the two or more suture openings have identical shapes.

17. The instrument of claim 16, wherein each of the perimeter edge portions generally has an oval shape.

18. The instrument of claim 16, wherein each of the perimeter edge portions are symmetrical about an axis of symmetry and extend along the axis of symmetry from a proximal end to a distal end, and wherein the distal end of the perimeter edge portion of a first of the two or more suture openings is proximal to the distal end of the perimeter edge portion of a second of the two or more suture openings.

19. The instrument of claim 17, wherein the axis of symmetry of the perimeter edge portion of the first of the two or more suture openings is not parallel to the axis of symmetry of the perimeter edge portion of the second of the two or more suture openings.

20. The instrument of claim 18, wherein both the axis of symmetry of the perimeter edge portion of the first of the two or more suture openings and the axis of symmetry of the perimeter edge portion of the second of the two or more suture openings are each not parallel to the longitudinal axis of any of the two or more shafts.

21. The instrument of claim 11, wherein the longitudinal axis of each of the two or more shafts are parallel.

22. The instrument of claim 11, further comprising a drive link, wherein a portion of the drive link is pivotably coupled to the portion of the lever, and wherein the proximal end of each of the two or more pushers is coupled to the drive link.

* * * * *